United States Patent
Fisher et al.

(10) Patent No.: US 9,951,114 B2
(45) Date of Patent: Apr. 24, 2018

(54) RECOMBINANT CANCER THERAPEUTIC CYTOKINE

(71) Applicant: Virginia Commonwealth University, Richmond, VA (US)

(72) Inventors: Paul B. Fisher, Richmond, VA (US); Praveen Bhoopathi, Richmond, VA (US); Swadesh K. Das, Richmond, VA (US); Luni Emdad, Richmond, VA (US); Devanand Sarkar, Richmond, VA (US); Upneet Sokhi, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/895,138

(22) PCT Filed: Jun. 4, 2014

(86) PCT No.: PCT/US2014/040793
§ 371 (c)(1),
(2) Date: Dec. 1, 2015

(87) PCT Pub. No.: WO2014/197535
PCT Pub. Date: Dec. 11, 2014

(65) Prior Publication Data
US 2016/0108101 A1    Apr. 21, 2016

Related U.S. Application Data

(60) Provisional application No. 61/830,814, filed on Jun. 4, 2013.

(51) Int. Cl.
*A61K 38/00*    (2006.01)
*C07K 14/00*    (2006.01)
*C07K 14/54*    (2006.01)

(52) U.S. Cl.
CPC .......... *C07K 14/5428* (2013.01); *C07K 14/54* (2013.01); *A61K 38/00* (2013.01); *C07K 2319/055* (2013.01)

(58) Field of Classification Search
CPC ............................ C07K 14/5428; C07K 14/54
See application file for complete search history.

(56) References Cited

U.S. PATENT DOCUMENTS

| 4,405,712 A | 9/1983 | Vande Woude et al. |
| 4,650,764 A | 3/1987 | Temin et al. |

(Continued)

FOREIGN PATENT DOCUMENTS

| WO | WO-89/05345 | 6/1989 |
| WO | WO-90/06997 | 6/1990 |

(Continued)

OTHER PUBLICATIONS

Al-Madhoun et al., "Evaluation of Human Thymidine Kinase 1 Substrates as New Candidates for Boron Neutron Capture Therapy," Cancer Res. 64(17): 6280 (2004).

(Continued)

*Primary Examiner* — Cherie M Stanfield
(74) *Attorney, Agent, or Firm* — Foley & Lardner LLP

(57) ABSTRACT

Recombinant therapeutic cytokines ("therakines") for the treatment of cancer are provided. The recombinant therakines include a truncated region of MDA-7/IL-24 ("M4") not normally found in nature that has anti-cancer activity and a secretory signal which causes secretion of the therakine from plasmid/virus transduced normal and cancer cells and interaction of the therakine to MDA-7/IL-24 receptors on adjacent, neighboring and distant cancer cells. Therakine interaction results in bystander killing of the target cancer cell as well as adjacent, neighboring and distant cancer cells.

2 Claims, 10 Drawing Sheets

(56) References Cited

U.S. PATENT DOCUMENTS

| | | | |
|---|---|---|---|
| 5,252,479 | A | 10/1993 | Srivastava |
| 6,451,571 | B1 | 9/2002 | Loeb et al. |
| 6,897,024 | B2 | 5/2005 | Bussemakers et al. |
| 7,247,297 | B2 | 7/2007 | Weichselbaum et al. |
| 7,321,030 | B2 | 1/2008 | Hamada |
| 7,364,727 | B2 | 4/2008 | Li et al. |
| 7,816,131 | B2 | 10/2010 | Hung et al. |
| 8,034,914 | B2 | 10/2011 | Hochberg |
| 2006/0134801 | A1* | 6/2006 | Chada .................... C07K 14/47 436/177 |
| 2008/0000264 | A1 | 1/2008 | Roberts et al. |
| 2008/0213220 | A1 | 9/2008 | Fisher et al. |
| 2009/0031164 | A1 | 1/2009 | Duron et al. |
| 2011/0136221 | A1 | 6/2011 | Black |
| 2013/0263296 | A1 | 10/2013 | Pomper et al. |

FOREIGN PATENT DOCUMENTS

| | | | |
|---|---|---|---|
| WO | WO-92/05266 | 4/1992 | |
| WO | WO-92/07573 | 5/1992 | |
| WO | WO-92/14829 | 9/1992 | |
| WO | WO-2004/031364 | 4/2004 | |
| WO | WO-2006/060680 | 6/2006 | |
| WO | WO 2006060680 A2 * | 6/2006 | ............ A61K 45/06 |
| WO | WO-2007/127951 | 11/2007 | |
| WO | WO-2008/112470 | 9/2008 | |

OTHER PUBLICATIONS

Berkner. "Development of adenovirus vectors for the expression of heterologous genes," Biotechniques 6: 616-626 (1988).

Blaese et al., "T Lymphocyte-Directed Gene Therapy for ADA-212 SCID: Initial Trial Results After 4 Years," Science 270: 475-479 (1995).

Cai et al., "The improved syntheses of 5-substituted 2'-[18F]fluoro-2'-deoxy-arabinofuranosyluracil derivatives ([18F]FAU, [18F]FEAU, [18F]FFAU, [18F]FCAU, [18F]FBAU and [18F]FIAU) using a multistep one-pot strategy," Nuclear Medicine and Biology 38(5): 659-666 (2011).

Chan et al., "Evaluation of F-18-labeled 5-iodocytidine (18 F-FIAC) as a new potential positron emission tomography probe for herpes simplex virus type 1 thymidine kinase imaging," Nuclear Medicine and Biology 38(7): 987-995 (2011).

Cotten et al., "High-efficiency receptor-mediated delivery of small and large (48 kilobase gene constructs using the endosome-disruption activity of defective or chemically inactivated adenovirus particles," Proc. Natl. Acad. Sci. USA 89(13): 6094-6098 (1992).

Danos et al., "Safe and efficient generation of recombinant retroviruses with amphotropic and ecotropic host ranges," Proc. Natl. Acad. Sci. USA 85(17): 6460-6464 (1988).

Dash et al., "Apogossypol derivative Bl-97Cl (Sabutoclax) targeting Mcl-I sensitizes prostate cancer cells to mda-7/IL-24-mediated toxicity." Proc. Natl. Acad. Sci. USA 108: 8785-8790 (2011).

Dash et al., "Developing an effective gene therapy for prostate cancer: new technologies with potential to translate from the laboratory into the clinic," Discov Med 11: 46-56 (2011).

Dash, R. et al., "mda-7/IL-24: a unique member of the IL-10 gene family promoting cancer-specific toxicity." Cytokine & Growth Factor Rev, 2010, 21:381-391.

Dash, R. et al., "Novel mechanism of MDA-7/IL-24 cancer-specific apoptosis through SARJ induction," Cancer Res. 74: 563-574 (2014).

Donahue et al., "Reduction in SIV replication in rhesus macaques infused with autologous lymphocytes engineered with antiviral genes," Nature Medicine 4(2):181-186 (1998).

Doronin et al., "Tissue-Specific, Tumor-Selective, Replication-Competent Adenovirus Vector for Cancer Gene Therapy," J. Virol. 75(7): 3314-3324 (2001).

Emdad, L. et al., "Melanoma differentiation associated gene-7/interleukin-24 reverses multidrug resistance in human colorectal cancer cells," Mol. Cancer Ther. 6: 2985-2994 (2007).

Fisher, P.B. et al., "Melanoma differentiation associated gene-7/interleukin-24 (mda-7/IL-24): novel gene therapeutic for metastatic melanoma." Toxicol & Applied Pharmacol 224: 300-307 (2007).

Fisher. "Is mda-7/IL-24 a 'magic bullet' for cancer?" Cancer Res 65: 10128-10138 (2005).

Freireich et al., "Quantitative comparison of toxicity of anticancer agents in mouse, rat, hamster, dog, monkey, and man," Cancer Chemother. Rep. 50(4): 219-44 (1966).

Gao, P. et al. "Secretable chaperone Grp 170 enhances therapeutic activity of a novel tumor suppressor, mda-7/IL-24." Cancer Res, 2008, 68: 3890-3898.

Geller et al., "A Defective HSV-1 Vector Expresses *Eschirichia coli* beta-galactosidase in Cultured Peripheral Neurons," Science 241: 1667-1669 (1988).

Gilad et al., "Artificial reporter gene providing MRI contrast based on proton exchange," Nature Biotechnology 25(2): 217-219 (2007).

Gilad et al., "MRI Reporter Genes," J. Nucl. Med. 49(12): 1905-1908 (2008).

Goldman et al., "Lentiviral Vectors for Gene Therapy of Cystic Fibrosis," Human Gene Therapy 10: 2261-2268 (1997).

Graham et al., "Manipulation of Adenovirus Vectors," Methods in Mol. Biol.: Gene Transfer and Expression Protocols 7: 109-127 (1991).

Greelish et al., "Stable restoration of the sarcoglycan complex in dystrophic muscle perfused with histamine and a recombinant adeno-associated viral vector," Nature Med. 5:439-443 (1999).

Gupta, P. et al., "BiP/GRP78 is an intracellular target for MDA-7/IL-24 induction of cancer-specific apoptosis." Cancer Res, 2006, vol. 66: 8182-91.

Hallenbeck et al., "A Novel Tumor-Specific Replication-Restricted Adenoviral Vector for Gene Therapy of Hepatocellular Carcinoma," Human Gene Therapy 10(10): 1721-1733 (1999).

Herzog et al., "Long-term correction of canine hemophilia B by gene transfer of blood coagulation factor IX mediated by adeno-associated viral vector," Nature Medicine 5(1): 56-63 (1999).

International Preliminary Report on Patentability for PCT/US2014/040793, dated Dec. 8, 2015.

International Search Report on PCT/US2014/040793 dated Nov. 3, 2014.

Iordanova et al., "In vivo magnetic resonance imaging of ferritin-based reporter visualizes native neuroblast migration," Neuroimage 59(2):1004-1012 (2012).

Jiang, H. et al., "Subtraction hybridization identifies a novel melanoma differentiation associated gene, mda-7, modulated during human melanoma differentiation, growth and progression." Oncogene, 1995, vol. 11: 2477-2486.

Jiang, H. et al., "The melanoma differentiation associated gene mda-7 suppresses cancer cell growth." Proc. Natl. Acad. Sci. USA 93(17): 9160-9165 (1996).

Jiang, H. et al., "Use of a sensitive and efficient subtraction hybridization protocol for the identification of genes differentially regulated during the induction of differentiation in human melanoma cells." Mol Cell Different 1: 285-299 (1993).

Kafri et al., "Sustained expression of genes delivered directly into liver and muscle by lentiviral vectors," Nature Genetics 17(3): 314-317 (1997).

Kurihara et al., "Selectivity of a replication-competent adenovirus for human breast carcinoma cells expressing the MUC1 antigen," J. Clin. Invest. 106: 763-771 (2000).

Lebedeva, I.V. et al., "Mechanism of in vitro pancreatic cancer cell growth inhibition by melanoma differentiation-associated gene-7/interleukin-24 and perillyl alcohol," Cancer Res 68: 7439-47 (2008).

Lee et al., "Selective Activation of Ceruloplasmin Promoter in Ovarian Tumors: Potential Use for Gene Therapy," Cancer Res. 64(5): 1788 (2004).

Li et al., "Assessment of Recombinant Adenoviral Vectors for Hepatic Gene Therapy," Human Gene Therapy 4:403-409 (1993).

Mocarski et al "Viral Vectors." Gluzman and Hughes (eds.). Cold Spring Harbor Laboratory, Cold Spring Harbor, N. U., 1988, pp. 78-84.

(56) References Cited

OTHER PUBLICATIONS

Muller et al., "Synthesis and evaluation of a C-6 alkylated pyrimidine derivative for the in vivo imaging of HSV1-TK gene expression," Nuclear Medicine and Biology 39(2): 235-246 (2012, in press 2011).

Onodera et al., "Development of Improved Adenosine Deaminase Retroviral Vectors," J. Virol. 72(3):1769-1774 (1998).

Piccini et al., "Vaccinia virus as an expression vector," Meth. Enzymology 153: 545-563 (1987).

Ramesh, R. et al., "Melanoma differentiation-associated gene 7 /interleukin (IL)-24 is a novel ligand that regulates angiogenesis via the IL-22 receptor," Cancer Res. 63:5105-5113 (2003).

Rodriguez et al., "Prostate Attenuated Replication Competent Adenovirus (ARCA) CN706: A Selective Cytotoxic for Prostate-specific Antigen-positive Prostate Cancer Cells," Cancer Res. 57(13): 2559-2563 (1997).

Sarkar et al., "Eradication of therapy-resistant human prostate tumors using a cancer terminator virus," Cancer Res 67: 5434-5442 (2007).

Sarkar, D. et al., "Melanoma differentiation associated gene-7 (mda-7)/IL-24: a 'magic bullet' for cancer therapy?" Expert Opin Biol Ther. 2007a; 7: 577-586.

Sauane, M. et al., Autocrine regulation of mda-7/IL-24 mediates cancer-specific apoptosis. Proc Natl Acad Sci USA 105: 9763-9768 (2008).

Sauane, M. et al., "N-glycosylation of MDA-7/IL-24 is dispensable for tumor cell-specific apoptosis and "bystander" antitumor activity," Cancer Res. 2006; 66: 11869-11877.

Shackleford et al., "Construction of a clonable, infectious, and tumorigenic mouse mammary tumor virus provirus and a derivative genetic vector," Proc. Natl. Acad. Sci. USA 85: 9655-9659 (1988).

Snyder et al., "Correction of hemophilia B in canine and murine models using recombinant adeno-associated viral vectors," Nature Medicine 5(1): 64-70 (1999).

Su, Z. et al., "Cloning and characterization of SARI (suppressor of AP-1, regulated by IFN)," Proc. Natl. Acad. Sci. USA 105: 20906-20911 (2008).

Su, Z. et al., "The cancer growth suppressor gene mda-7 selectively induces apoptosis in human breast cancer cells and inhibits tumor growth in nude mice." Proc Natl Acad Sci USA 95: 14400-14405, 1998.

Su, Z. et al., "Unique aspects of mda-7/IL-24 anti tumor bystander activity: establishing a role for secretion of MDA-7 /IL-24 protein by normal cells." Oncogene 24: 7552-7566 (2005).

Tian, H. et al., "Critical role of lysine 123 in the ubiquitin-mediated degradation of MDA-7/IL-24," J Interferon Cytokine Res. 32(12): 575-582 (2012).

Tong, A.W. et al., "Intratumoral injection of INGN 241, a nonreplicating adenovector expressing the melanoma-differentiation associated gene-7 (mda-7/IL24): biologic outcome in advanced cancer patients." Mol Ther 11: 160-172 (2005).

Venkatesan et., "The potential of celecoxib-loaded hydroxyapatite-chitosan nanocomposite for the treatment of colon cancer," Biomaterials 32(15): 3794-3806 (2011).

Wang et al., "Sustained correction of bleeding disorder in hemophilia B mice by gene therapy," Proc. Natl. Acad. Sci. USA 96: 3906-3910 (1999).

Xu, S. et al., "Stabilization of MDA-7/IL-24 for colon cancer therapy," Cancer Lett. 335(2):421-430 (2013).

Yacoub, A. et al., "MDA-7/IL-24 plus radiation enhance survival in animals with intracranial primary human GBM tumors." Cancer Biol Ther, 2008, vol. 7: 917-933.

Zabner et al., "Safety and efficacy of repetitive adenovirus-mediated transfer of CFTR cDNA to airway epithelia of primates and cotton rats," Nature Genetics 6:75-83 (1994).

Extended European Search Report issued on EP Application 14807031.1, dated Nov. 17, 2016.

Huang et al., "Genomic structure, chromosomal localization and expression profile of a novel melanoma differentiation associated (mda-7) gene with cancer specific growth suppressing and apoptosis inducing properties," 2001 Oncogene 20(48): 7051-7063.

\* cited by examiner

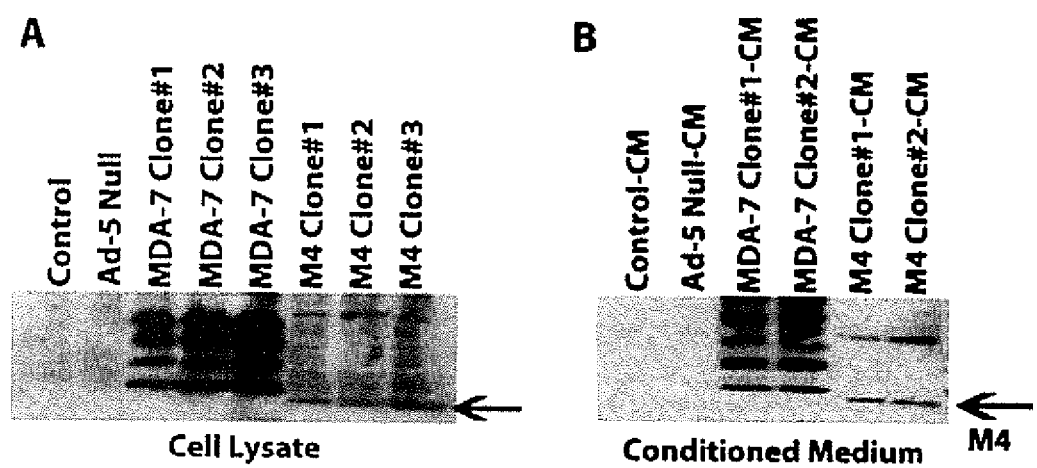
Figure 2A and B

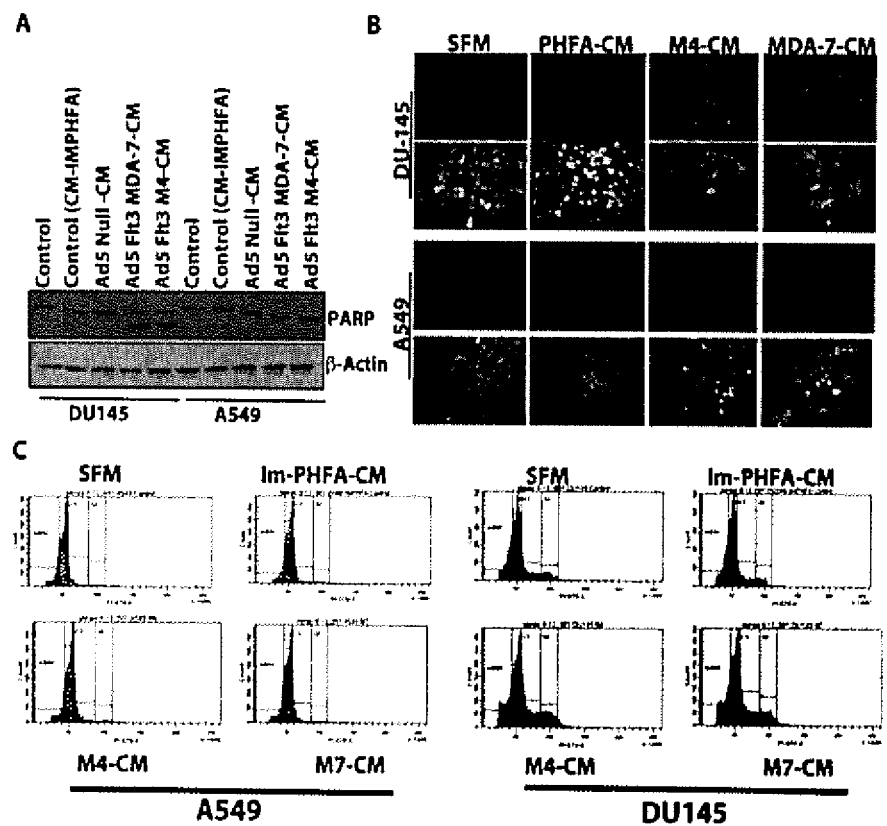
Figure 3A-C

A.    B.
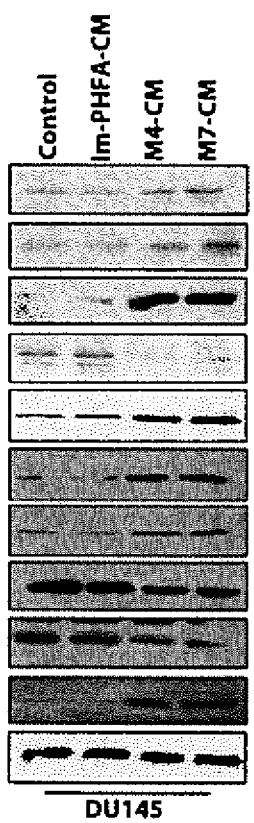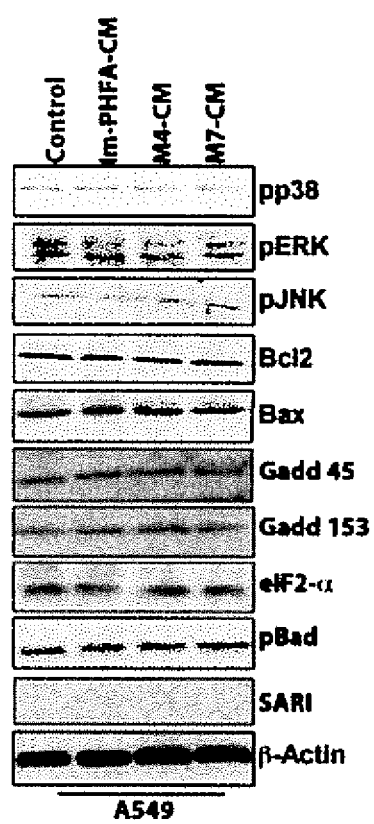
Figure 4A and B

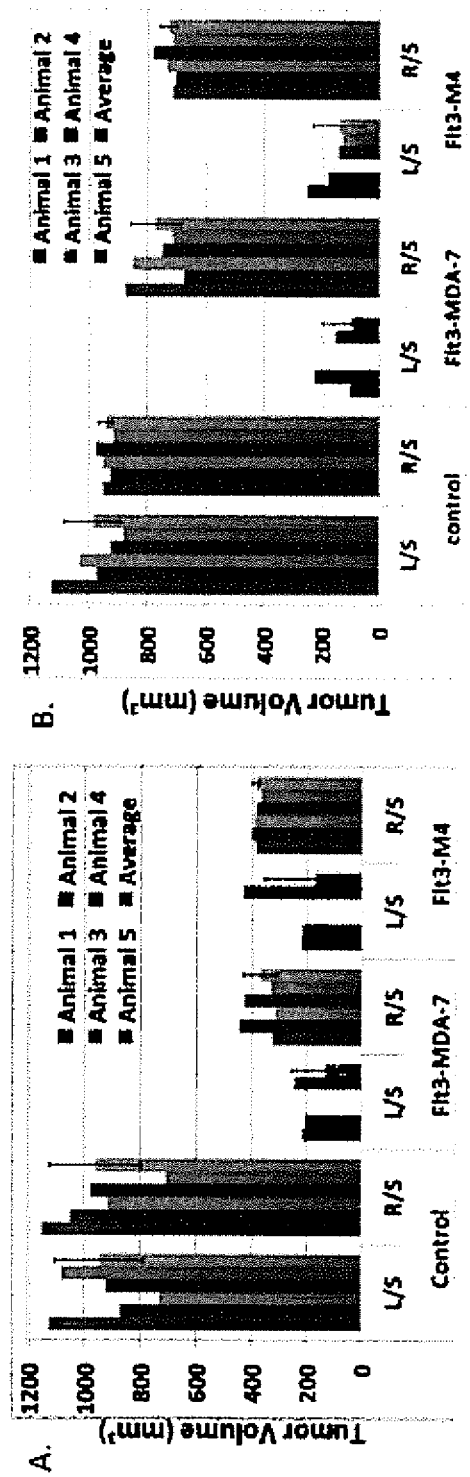
Figure 5A and B

A.

ESCYLVHTLLEFYLKTVFKNYHNRTVEVRTLKSFSTLANNFVLIVSQLQPSQENE
MFSIRDSAHRRFLLFRRAFKQLDVEAALTKALGEVDILLTWMQKFYKL (SEQ ID NO: 1)

B.

GAG AGC TGT TAC CTT GTC CAC ACC CTG CTG GAG TTC TAC TTG AAA
ACT GTT TTC AAA AAC TAC CAC AAT AGA ACA GTT GAA GTC AGG ACT
CTG AAG TCA TTC TCT ACT CTG GCC AAC AAC TTT GTT CTC ATC GTG TCA
CAA CTG CAA CCC AGT CAA GAA AAT GAG ATG TTT TCC ATC AGA GAC
AGT GCA CAC AGG CGG TTT CTG CTA TTC CGG AGA GCA TTC AAA CAG
TTG GAC GTA GAA GCA GCT CTG ACC AAA GCC CTT GGG GAA GTG GAC
ATT CTT CTG ACC TGG ATG CAG AAA TTC TAC AAG CTC TGA (SEQ ID NO: 2)

C.

MTVLAPAWSPTTYLLLLLLLSGS (SEQ ID NO: 3)

D.

ATG ACA GTG CTG GCG CCA GCC TGG AGC CCA ACA ACC TAT CTC CTC
CTG CTG CTG CTG CTG AGC GGA TCC (SEQ ID NO: 4)

MTVLAPAWSPTTYLLLLLLLLSGSESCYLVHTLLEFYLKTVFKNYHNRTVEVRTL
KSFSTLANNFVLIVSQLQPSQENEMFSIRDSAHRRFLLFRRAFKQLDVEAALTKAL
GEVDILLTWMQKFYKL (SEQ ID NO: 5)

B.

ATG ACA GTG CTG GCG CCA GCC TGG AGC CCA ACA ACC TAT CTC CTC
CTG CTG CTG CTG CTG AGC GGA TCC GAG AGC TGT TAC CTT GTC CAC
ACC CTG CTG GAG TTC TAC TTG AAA ACT GTT TTC AAA AAC TAC CAC
AAT AGA ACA GTT GAA GTC AGG ACT CTG AAG TCA TTC TCT ACT CTG
GCC AAC AAC TTT GTT CTC ATC GTG TCA CAA CTG CAA CCC AGT CAA
GAA AAT GAG ATG TTT TCC ATC AGA GAC AGT GCA CAC AGG CGG TTT
CTG CTA TTC CGG AGA GCA TTC AAA CAG TTG GAC GTA GAA GCA GCT
CTG ACC AAA GCC CTT GGG GAA GTG GAC ATT CTT CTG ACC TGG ATG
CAG AAA TTC TAC AAG CTC TGA (SEQ ID NO: 6)

Figure 12A and B

RECOMBINANT CANCER THERAPEUTIC CYTOKINE

CROSS-REFERENCE TO RELATED APPLICATIONS

This application is a U.S. national stage application under 35 U.S.C. § 371 of International Application No. PCT/US2014/040793, filed Jun. 4, 2014, which claims the benefit of U.S. Provisional Application No. 61/830,814, filed Jun. 4, 2013, which are incorporated herein by reference in their entireties.

BACKGROUND OF THE INVENTION

Field of the Invention

The invention generally relates to novel recombinant therapeutic cytokines ("therakines") for the treatment of cancer. In particular, the invention provides recombinant cytokines which include i) an "M4" region of MDA-7/IL-24 that has anti-cancer activity and ii) a secretory signal which permits the therakine to be secreted from plasmid/virus transduced normal or cancer cells and then bind to and exhibit a bystander cell-killing effect in neighboring cancer cells.

Background of the Invention

IL-10 gene family member melanoma differentiation associated gene-7/Interleukin-24 (MDA-7/IL-24) displays profound broad-spectrum anti-cancer therapeutic activity, both in vitro in primary and established human cancer cells lines, in vivo in nude mouse and transgenic animal models and in a Phase I/II clinical trial in patients with advanced cancers (including carcinomas and melanomas). A major contributing factor in the ability of MDA-7/IL-24 to show such robust anti-cancer activity in viva is its profound "bystander" antitumor activity upon secretion from plasmid/virus transduced cells. During secretion from transduced cell, a 47 amino acid secretory signal is cleaved from MDA-7/IL-24. The secreted form of the protein interacts with dimeric receptors, e.g. IL-20R1/IL-20R2, IL-22R/IL-20R2 and IL-20R1/IL-22R on the surface of neighboring cancer cells it encounters after secretion, thereby directly inducing growth suppression, apoptosis and toxic autophagy in the tumor cells. Secreted MDA-7/IL-24 protein also induces secondary anti-tumor effects by inhibiting tumor angiogenesis and promoting an anti-tumor immune response. Remarkably, MDA-7/IL-24 lacks harmful effects on normal cells or tissues.

There is a need in the art to further extend knowledge concerning the mechanism of action of MDA-7/IL-24 and to develop alternative forms of this protein. Especially desirable would be forms of the protein that retain full bystander activity, and which are readily administrable as proteins/polypeptide, or amenable to incorporation into recombinant constructs (e.g. vectors) for administration to cancer patients.

SUMMARY OF THE INVENTION

This disclosure describes a novel bioactive synthetic cytokine, a "therakine", which unexpectedly displays potent "bystander" anti-cancer activity in tumor cells containing dimeric MDA-7/IL-24 receptors. This new cytokine was discovered as a result of mutational analysis that was performed to elucidate the role of specific regions of MDA-7/IL-24 in promoting cancer cell death. The investigations resulted in identification of "M4", a region of MDA-7/IL-24 containing amino acids 104 to 206 of the MDA-7/IL-24 protein (103 amino acids total). Notably, M4 lacks 103 amino terminal amino acids, including the 47 amino acid secretory region (secretory motif) of MDA-7/IL-24. This truncated, mutant form of the MDA-7/IL-24 was as potent as the full-length protein in inducing cancer-specific cell death in cells in which it is produced (Dash et al. Cytokine & Growth Factor Reviews; 21 (2010) 381-391). Although this observation was exciting, the utility of the M4 mutant as a therapeutic for cancer was assumed to be limited because it lacks 103 amino terminal amino acids, including the 47 amino acid secretory region. M4 is thus not secreted and is therefore incapable of exhibiting classical "bystander" anti-tumor activity on its own. Instead, the use of M4 as an anticancer agent would require direct delivery of the molecule to the interior of a cancer cell in order to benefit from its anti-cancer activity.

The "bystander" antitumor activity of MDA-7/IL-24 depends critically on cytokine signaling through receptors on the surface of cancer cells. Productive interaction between MDA-7/IL-24 and receptors requires a particular three-dimensional configuration of MDA-7/IL-24 that results in precise positioning of residues on the surface of the protein. While in theory M4 could be modified to be secreted, it was believed that the resulting polypeptide, lacking 103 amino acids of the native MDA-7/IL-24, would surely lack the preferred shape to interact with surface receptors and hence would not be capable of exhibiting the bystander effect. However, when this hypothesis was tested, the results were surprising and unanticipated in that addition of a secretory signal to M4 resulted in a recombinant molecule, which displayed "bystander" activity equivalent to that of full length MDA-7/IL-24. Like full length MDA-7/IL-24, this truncated and modified recombinant polypeptide exhibits direct and distant killing of cancer cells, both in vitro and in vivo; activity in animal models shows that the recombinant secreted protein is active and can reach distant tumors through the circulation. In contrast to MDA-7/IL-24, which promotes its own production in cells, M4 does not induce this effect, but like MDA-7/IL-24, M4 does induce production of SARI (Suppressor of AP-1, regulated by Interferon) (Su et al., Proc Natl Acad Sci USA; 105 (2012) 20906-20911; Dash et al., Cancer Res; 74 (2014) 563-574), which is required for cell killing by MDA-7/IL-24.

This novel "therakine" (therapeutic cytokine) thus represents a new therapeutic molecule for the treatment of diverse cancers and is a paradigm shifting observation with respect to requirements for cytokine activity. In particular, this new truncated version of MDA-7/IL-24, which does not normally exist innately in nature, can be readily incorporated into heterologous constructs designed for targeted delivery to cancer cells, as described in detail herein. The shorter length of the polypeptide is advantageous in terms of production and manufacturing, and yet retains the most desirable characteristics of the natural parent molecule, MDA-7/IL-24. Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide recombinant cytokines comprising a fragment of MDA-7/IL-24 that i) has antitumor activity and ii) interacts with MDA-7/IL-24 receptors on the surface of cancer cells; and a secretory leader sequence. In some aspects, the fragment of MDA-7/IL-24 comprises amino acids 104 to 206 of MDA-7/IL-24 (SEQ ID NO: 1). The secretory leader sequence may be a heterologous secretory leader sequence, for example, the Flt3 sequence of SEQ ID NO: 3. In some aspects, an amino acid sequence of the recombinant cytokine is represented by SEQ ID NO: 5.

The invention further provides nucleic acid sequences encoding a recombinant cytokine comprising a fragment of MDA-7/IL-24 that i) has antitumor activity and ii) interacts with MDA-7/IL-24 receptors on the surface of cancer cells; and a secretory leader sequence. In some aspects, the fragment of MDA-7/IL-24 comprises amino acids 104 to 206 of MDA-7/IL-24 (SEQ ID NO: 1) encoded by the nucleic acid represented by SEQ ID NO: 2. The secretory leader sequence may be a heterologous secretory leader sequence such as the Flt3 sequence (SEQ ID NO: 3) encoded by the nucleic acid represented by SEQ ID NO: 4. In some aspects, the nucleic acid sequence is represented in SEQ ID NO: 6.

The invention also provides recombinant vectors comprising a nucleic acid sequence encoding a recombinant cytokine comprising a) a fragment of MDA-7/IL-24 that i) has antitumor activity and ii) interacts with MDA-7/IL-24 receptors on the surface of cancer cells; and b) a secretory leader sequence, wherein said nucleic acid sequence is operably linked to a promoter. In some aspects, the fragment of MDA-7/IL-24 comprises amino acids 104 to 206 of MDA-7/IL-24 (SEQ ID NO: 1) encoded by the nucleic acid represented by SEQ ID NO: 2. The secretory leader sequence may be a heterologous secretory leader sequence such as the Flt3 sequence (SEQ ID NO: 3) encoded by the nucleic acid represented by SEQ ID NO: 4. In some aspects, the nucleic acid sequence is represented in SEQ ID NO: 6. The recombinant vector may further comprise a cancer specific or cancer selective promoter operationally linked to the nucleic acid encoding the recombinant cytokine. The recombinant vector is, in some cases, a viral vector such as, for example, an adenoviral vector, a lentiviral vector, a herpes simplex virus, a measles virus, and a vaccinia virus. In other aspects, the recombinant vector comprises at least one additional gene of interest encoding one or more of an anticancer agent, an imaging agent and at least one gene that is required for viral replication. The at least one additional gene of interest is also generally operably linked to a promoter. The promoters that are used in the recombinant vector may be, for example, a truncated CCN1 promoter, an mda-9/syntenin promoter, a PEG-Prom, an AEG-1-Prom, or a CMV promoter.

The invention further provides nanoparticles comprising a nucleic acid sequence encoding a recombinant cytokine comprising a fragment of MDA-7/IL-24 that i) has antitumor activity and ii) interacts with MDA-7/IL-24 receptors on the surface of cancer cells; and a secretory leader sequence. The nucleic acid sequence is operably linked to a promoter.

The invention also provides methods of treating or preventing cancer and/or cancer metastasis in a subject in need thereof, comprising
administering to said subject a recombinant cytokine comprising a fragment of MDA-7/IL-24 that i) has antitumor activity and ii) interacts with MDA-7/IL-24 receptors on the surface of cancer cells; and a secretory leader sequence. In some aspects, the recombinant cytokine has an amino acid sequence as set forth in SEQ ID NO: 1. In some aspects, the recombinant cytokine is administered as a protein, e.g. having an amino acid sequence as set forth in SEQ ID NO: 1. In other aspects, the recombinant cytokine is administered by administering a vector comprising a nucleic acid sequence that encodes the recombinant cytokine, e.g. a nucleic acid sequence as set forth in SEQ ID NO: 2. In some cases, the cancer is selected from the group consisting of osteosarcoma, ovarian carcinoma, breast carcinoma, melanoma, hepatocarcinoma, lung cancer, brain cancer, colorectal cancer, hematopoietic cell cancer, prostate cancer, cervical carcinoma, retinoblastoma, esophageal carcinoma, bladder cancer, neuroblastoma, renal cancer, gastric cancer, and pancreatic cancer.

The invention also provides recombinant cDNAs comprising the nucleotide sequence set forth as SEQ ID NO: 1. The recombinant cDNAs do not encode full length MDA-7/IL-24.

The invention also provides isolated recombinant cytokines comprising a fragment of MDA-7/IL-24 that i) has antitumor activity and ii) interacts with MDA-7/IL-24 receptors on the surface of cancer cells. In some aspects, an amino acid sequence of the isolated recombinant cytokine comprises SEQ ID NO: 1. The isolated recombinant cytokine may further comprise a secretory leader sequence. In some aspects, an amino acid sequence of the isolated recombinant cytokine comprises SEQ ID NO: 3.

The invention further provides a composition comprising the isolated recombinant cytokine as described above.

BRIEF DESCRIPTION OF THE DRAWINGS

FIGS. 2A and B. MDA-7/IL-24 and M4 are present in conditioned medium (CM). (A) Western blot analysis of MDA-7/IL-24 and M4 in total cellular lysates. (B) Western blot analysis of MDA-7/IL-24 and M4 in CM. Experiment was repeated at least three times and representative images of Western blots are shown.

FIG. 3A-C. Secreted MDA-7/IL-24 and M4 induce apoptosis in DU145 but not in A549 cells. (A) Western blot analysis of DU145 or A549 cells; (B) TUNEL assay of DU145 or A549 cells; (C) DNA content of DU145 or A549 cells as measured by FACS. All the experiments were repeated at least three times and representative images are shown.

FIGS. 4A and B. Western blot analysis of pro- and anti-apoptotic molecules secreted by DU145 and A549 cells after exposure to MDA-7/IL-24 and M4. A, DU145 cells; B, A549 cells. Experiment was repeated at least three times and representative images of Western blots are shown.

FIGS. 5 A and B. Tumor volume reduction in vivo after subcutaneous tumor cell implants: secreted MDA-7/IL-24 and M4 promotes profound 'bystander' activity in DU145 cells with a minimal effect on A549 cells. A, DU145 cells implanted on both sides of mice; B, DU145 cells implanted on the left side and A549 cells implanted on the right side. Tumors were treated as indicated with Flt3-MDA-7 or Flt3-M4 constructs.

FIG. 11 A-D. A, amino acid sequence of M4 (SEQ ID NO: 1); B, nucleotide sequence encoding M4 (SEQ ID NO: 2); C, amino acid sequence of exemplary secretion signal (from Flt3, SEQ ID NO: 3); D, nucleotide sequence encoding Flt3 secretion signal (SEQ ID NO: 4).

FIGS. 12 A and B. A, amino acid sequence of an exemplary recombinant M4 therakine (SEQ ID NO: 5); B, nucleotide sequence encoding the exemplary recombinant M4 therakine shown in A (SEQ ID NO: 6).

DETAILED DESCRIPTION

Figure 1:
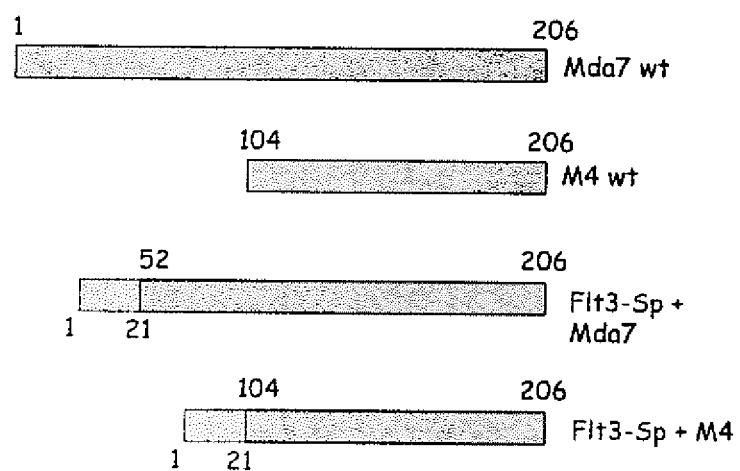
FIG. 1. Schematic representation of Flt3-Mda-7 and Flt3-M4 construction.

Provided herein are new recombinant therapeutic cytokines ("therakines") which are used, for example, in the treatment of cancer. The recombinant therakines comprise an "M4" region or fragment or portion of MDA-7/IL-24, e.g. the contiguous amino acid residues from approximately residue 104 to approximately residue 206, inclusive (e.g. generally about 103 amino acids in total length). In some aspects, M4 includes amino acids 104 to 206, inclusive, of MDA-7/IL-24. The molecules are referred to herein as "recombinant M4 therakines" and/or by equivalent terminology. The primary amino acid sequence of an exemplary truncated segment of MDA-7/IL-24 is set forth in SEQ ID NO: 1 (FIG. 11A). In some aspects, the recombinant M4 therakine includes a leader sequence that causes secretion of the polypeptide (e.g. a "secretory" or "signal" sequence) that is attached at the amino terminus of the polypeptide. The primary amino acid sequence of an exemplary secretory sequence (that of the Flt3 ligand) is set forth in SEQ ID NO: 3 (FIG. 11C). The primary amino acid sequence of an exemplary recombinant therakine comprising M4 and the Flt3 secretory sequence is presented in SEQ ID NO: 5 (FIG. 12A). Exemplary nucleic acids encoding the peptides/polypeptides of SEQ ID NOS: 1, 3 and 5 are set forth in SEQ ID NOS: 2, 4 and 6, respectively (see FIGS. 11 and 12).

Those of skill in the art will recognize that the primary amino acid sequence of the peptides and polypeptides of the M4 component of the recombinant M4 therakine need not be the exact sequence that is set forth in SEQ ID NO: 1. Various modifications of those sequences can be tolerated in the therakine, so long as full bystander activity (bystander activity comparable to or equal to or greater than that of MDA-7/IL-24) is retained by the translated polypeptide. For example, at least 25, 30, 35, 40, 45, 50, 55, 60, 65, 70, 75, 80, 85, 90, 95, or 100% of the bystander activity of MDA-7/IL-24 is retained, and in some cases, the activity of the recombinant therakine may exceed that of native MDA-7/IL-24, e.g. may be 25, 30, 35, 40, 45, 50, 55, 60, 65, 70, 75, 80, 85, 90, 95, or 100% (2-fold) greater, or more (e.g. about 2.0, 2.5, 3.0, 3.5, 4.0, 4.5, 5.0, 6.0, 6.5, 7.0, 7.5, 8.0, 8.5, 9.0, 9.5 or, 10 or more (e.g. up to 100 or 500 or even 1000 fold greater, including fold-values of all integers in between these ranges).

The recombinant M4 therakines thus not only function to kill cancer cells in which they are expressed (direct killing), but they also advantageously exhibit the ability to be secreted from both normal and cancer cells in which they are produced and to interact with and kill or damage adjacent, nearby and distant cancer cells, at least those which display canonical MDA-7/IL-24 receptors. Thus, the recombinant M4 therakines surprisingly do have the ability to interact with MDA-7/IL-24 receptors and as a result, they have "bystander" or "distant killing" activity. However, the anti-cancer activity of the therakine is not limited to bystander activity, but typically also includes the ability to induce production of Suppresssor of AP-1 regulated by interferon (SARI), at the same or similar level as MDA-7/IL-24, e.g., at least 25, 30, 35, 40, 45, 50, 55, 60, 65, 70, 75, 80, 85, 90, 95, or 100% or more of the level of SARI activity induced by MDA-7/IL-24.

Those of skill in the art are familiar with methods to measure activity levels of cytokines, e.g. levels of receptor binding, levels of cancer cell killing, levels of SARI induction, amount of tumor volume reduction, etc. Exemplary methods are described in the Examples section below.

Modifications of the sequences disclosed herein (e.g. of the M4 component of the recombinant M4 therakine, and/or of a secretory sequence such as that or SEQ ID NO: 3, and/or of the exemplary recombinant M4 therakine such as that of SEQ ID NO 5) include but are not limited to: conservative or non-conservative amino acid substitutions; changes in the sequence to facilitate manipulation, production and/or isolation and purification of the polypeptide (e.g. the addition of tagging sequences such as His tags, or of detectable residues such as tyrosine); or inclusion of residues that are introduced as a result of changes in the encoding nucleic acid sequence for ease of cloning (e.g. introduction of restriction sites, etc, into the encoding nucleic acid); or amino acid sequence changes to increase or decrease solubility; changes in sequences which are susceptible to proteolytic cleavage to promote stability of the polypeptide; or the introduction of proteolytic cleavage sites to facilitate or foster desired patterns of cleavage; addition or removal of from about 1 to about 5 amino acids (e.g. 1, 2, 3, 4, or 5) from the amino and/or carboxyl termini, etc. In addition, various mutations that can increase the activity of M4 may be introduced, e.g. mutation of lysine at position 123, which is involved in ubiquitination and consequent degradation, to e.g. R or another suitable residue to render the protein less susceptible to degradation but maintain (or even increase) activity or effective activity [see Tian H, Li L, Zhang B, Di J, Chen F, Li H, Liu J, Pei D, Zheng J. Critical role of lysine 123 in the ubiquitin-mediated degradation of MDA-7/IL-24. J Interferon Cytokine Res. 2012 December; 32(12):575-582]. Generally, a recombinant M4 therakine variant will be or will comprise an amino acid sequence that has at least about 50, 55, 60, 65, 70, 75, 80, 85, 90, 95, 96, 97, 98, or 99% sequence identity, or at least about 50, 55, 60, 65, 70, 75, 80, 85, 90, 95, 96, 97, 98, or 99% sequence similarity, to the amino acid sequence presented in SEQ ID NO: 1, when aligned using a known identity/similarity calculating program. As a caveat, the therakine sequence may be a sequence that is longer than that which is set forth in SEQ ID NO: 1 but the longer sequence is not MDA-7/IL-24, although is may have the same number of amino acids or even more amino acids than MDA-7/IL-24. In sequences longer than SEQ ID NO: 1, SEQ ID NO: 1 is flanked by one or more heterologous, non-native amino acids or amino acid sequences (amino acids or amino acid sequences that do not flank SEQ ID NO: 1 in nature) at one or both of the amino and carboxyl termini.

Other means of increasing the effective activity of the M4 therakine are also contemplated. For example, "small molecule" stabilizers such as SC144 may be used [see Xu S, Oshima T, Imada T, Masuda M, Debnath B, Grande F, Garofalo A, Neamati N. Stabilization of MDA-7/IL-24 for colon cancer therapy. Cancer Lett. 2013 Jul. 28; 335(2):421-30]. While the activity of an individual molecule of M4 therakine may or may not be increased due to such stabilizers (either mutations of the sequence or by interactions with small molecules), the effective activity (the amount or level of activity that is observed or measured) may increase due to the increased lifetime of the therapeutic molecules.

With respect to the nucleic acid sequences disclosed herein, those of skill in the art will recognize that the particular sequences are exemplary, because, for example, the genetic code is redundant so that many other sequences would encode both the recombinant M4 therakine polypeptides that are disclosed explicitly herein, and the modified active variants described above. For example, the sequences may be modified according to preferred codon usages for particular species of animals (e.g. experimental animal models), or for ease of cloning (e.g. to introduce restriction sites or sequences which base pair with vector sequences, to introduce or remove stop and/or start codons, or for any other reason, e.g. the nucleic acid sequence may be modified to encode changes to the amino acid sequence as described above, for example, to decrease degradation through ubiquitination by mutation of Lys 123, or to encode a stabilizing small molecule, etc. Generally, variants of SEQ ID NO: 2 have at least about 50, 55, 60, 65, 70, 75, 80, 85, 90, 95, 96, 97, 98, or 99% sequence identity, or at least about 50, 55, 60, 65, 70, 75, 80, 85, 90, 95, 96, 97, 98, or 99% sequence similarity, to SEQ ID NO: 2, when aligned using a known identity/similarity calculating program. Further, nucleic acid sequences which are longer than that which is set forth in SEQ ID NO: 2 are encompassed, so long as at least one region or portion of the sequence encodes a sequence with the level of homology or similarity to SEQ ID NO: 2 indicated herein, with the caveat that such nt sequences do not encode a full length MDA-7/IL-24. Lengthier sequence may, for example, encode 2 or more copies of a sequence that encodes the M4 cytokine. All such nucleotide sequences are encompassed by the present invention, including DNA, cDNA, mRNA, DNA/RNA hybrids, etc. whether single or double stranded. mRNA sequences encoding the therakine include at least one heterologous nucleotide or nucleotide sequence that is not present in native or natural mRNAs encoding the parent MDA-7/IL-24, e.g. flanking the coding sequence such as at either or at both the 3' and 5' termini.

The present invention also provides cDNA sequences encoding the M4 therakine. The sequences of the cDNAs are fragments (portions, segments, etc.) of the full-length cDNA that encodes the parent molecule, MDA-7/IL-24, the parent molecules being encoded by a gene with multiple introns (Huang et al., 2001. Oncogene 20(48): 7051-63). The M4 start sequence (GAGAGCT) is positioned near the beginning of exon 5 such that exons 5, 6 and 7 are common between the parent MDA-7 and M4. The genomic sequence that encompasses M4 thus has 2 introns, one between exons 5 and 6, and the second between exons 6 and 7. Neither intron is present in the cDNA. One exemplary cDNA sequence is presented in SEQ ID NO: 1. mRNA sequences translated from this cDNA are also encompassed by the invention.

In one aspect, the secretory signal of the recombinant M4 therakine is the exemplary Flt3 secretory sequence (SEQ ID NO: 3). However, many other signal sequences may also be used in the practice of the invention, including but not limited to: secretory signals from molecules including the melanoma differentiation associated gene-7/Interleukin-24 endogenous secretory peptide, interferon gamma (IFNγ), interleukin-8 (IL-8), matrix metalloproteinase-14 (MMP-14), transforming growth factor beta (TGF-β), insulin-like growth factor-binding protein 2 (IGFBP2), Dickkopf-related protein 1 (DKK1), secreted protein acidic and rich in cysteine (SPARC), secreted phosphoprotein 1 (SPP1) and interleukin-12 (IL-12), interleukin-10 (IL-10), signal peptide Gaussia Luciferase (sp-Gluc), etc. Any secretory leader sequence may be employed, so long as the final recombinant M4 therakine retains bystander cancer cell killing activity as described herein.

The invention also comprises methods of using the recombinant M4 therakine described herein. Exemplary uses include but are not limited to its use for treating cancer in a patient or subject in need thereof, and its use in manufacturing a medicament for treating cancer. In one aspect, in order to be used for treatment methods, nucleic acid sequences encoding the therakine are incorporated into a vector that is suitable for administration to a subject. Within the vector, the recombinant M4 therakine is operably linked to at least one element such as a promoter and/or other expression-related element (e.g. an enhancer, etc.) that drives expression of the therakine after administration, e.g. that drives or promotes or causes expression within the subject to whom the vector is administered, particularly within cancer cells in the subject. Suitable vectors that may be used for this purpose are described below, as well as suitable promoters and other elements that cause (drive, facilitate, etc.) productive transcription and translation of the recombinant M4 therakine, i.e., transcription into mRNA that is translated into an active gene product, i.e. a secretable recombinant M4 polypeptide with bystander activity. In another aspect, the therakine is administered as a protein.

Vectors

Vectors which may be used in the practice of the invention include both viral and non-viral vectors. Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. branched PEI)-DNA complexes; various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc).

In addition, viral vectors may be employed. Exemplary viral vectors include but are not limited to: bacteriophages, various baculoviruses, retroviruses, and the like. Those of skill in the art are familiar with viral vectors that are used in "gene therapy" applications, which include but are not limited to: Herpes simplex virus vectors (Geller et al., Science, 241:1667-1669 (1988)); vaccinia virus vectors (Piccini et al., Meth. Enzymology, 153:545-563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., Proc. Natl. Acad. Sci. USA, 85:6460-6464 (1988); Blaese et al., Science, 270:475-479 (1995); Onodera et al., J. Viral., 72:1769-1774 (1998)); adenovirus vectors (Berkner, Biotechniques, 6:616-626 (1988); Cotten et al., Proc. Natl. Acad. Sci, USA, 89:6094-6098 (1992); Graham et al., Meth. Mol. Biol., 7:109-127 (1991); Li et al., Human Gene Therapy, 4:403-409 (1993); Zabner et al., Nature Genetics, 6:75-83 (1994)); adeno-associated virus vectors (Goldman et al., Human Gene Therapy, 10:2261-2268 (1997); Greelish et al., Nature Med., 5:439-443 (1999); Wang et al., Proc. Natl. Acad. Sci. USA, 96:3906-3910 (1999); Snyder et al., Nature Med., 5:64-70 (1999); Herzog et al., Nature Med., 5:56-63 (1999)); retrovirus vectors (Donahue et al., Nature Med., 4:181-186 (1998); Shackleford et al., Proc. Natl. Acad. Sci. USA, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., Nature Genetics, 17:314-317 (1997), as well as viruses that are replication-competent conditional to a cancer cell such as oncolytic herpes virus NV 1066 and vaccinia virus GLV-1h68, as described in United States patent application 2009/0311664. In particular, adenoviral vectors may be used, e.g. targeted viral vectors such as those described in published United States patent application 2008/0213220. In addition, various cancer-specific conditionally replication competent viruses, in which replication is controlled by the PEG-Prom, may be employed, as may viral (or other) vectors in which expression is regulated by the tCCN1-Prom, hTERT-Prom, mda-9-Prom, various cancer subtype-specific promoters, etc., as indicated below.

Those of skill in the art will recognize that the choice of a particular vector will depend on the details of its intended use. Typically, one would not use a vector that integrates into the host cell genome due to the risk of insertional mutagenesis, and would design vectors so as to avoid or minimize the occurrence of recombination within a vector's nucleic acid sequence or between vectors. The constructs and vectors may be produced using known recombinant technology or by synthetic (e.g. chemical) means.

Host cells which contain the recombinant M4 therakine and vectors encoding the recombinant M4 therakine are also encompassed, e.g. in vitro cells such as cultured cells, or bacterial or insect cells which are used to store, generate or manipulate the vectors, and the like, and/or cells that are in vivo (e.g. in a recipient to whom the recombinant M4 therakine or vectors encoding the recombinant M4 therakine have been administered Promoters The recombinant M4 therakine polypeptides of the invention are generally produced by vectors which include at least one transcribable element (e.g., a gene composed of a nucleic acid sequence that encodes a recombinant M4 therakine) that is operably connected or linked to one or more elements (such as a promoter, one or more enhancers sequences, etc.) that drive transcription and/or translation. "Operably linked" refers to an element being located or positioned within a recombinant construct so as to interact with an encoding nucleotide sequence of interest (e.g., encoding an M4 therakine) in a manner that results in successful transcription and/or translation of the nucleic acid. If the vector is a DNA vector, transcription from the construct into mRNA occurs; if the vector is an RNA vector, translation occurs from the construct. In some aspects, one element that drives expression is a promoter that is specific or selective for driving expression of the recombinant M4 therakine within cancer cells. Expression of the transcribable or translatable element may be inducible or constitutive, and suitable cancer selective/specific promoters (and or promoter/enhancer sequences) that may be used include but are not limited to: PEG-PROM (e.g. as described in U.S. patent application Ser. No. 13/881,777), astrocyte elevated gene 1 (AEG-1) promoter, survivin-Prom, human telomerase reverse transcriptase (hTERT)-Prom, hypoxia-inducible promoter (HIF-1-alpha), DNA damage inducible promoters (e.g. GADD promoters), metastasis-associated promoters (metalloproteinase, collagenase, melanoma differentiation associated gene-9, etc.), ceruloplasmin promoter (Lee et al., Cancer Res Mar. 1, 2004 64; 1788), mucin-1 promoters such as DF3/MUC1 (see U.S. Pat. No. 7,247,297), Hex11 promoter as described in US patent application 2001/00111128; prostate-specific antigen enhancer/promoter (Rodriguez et al. Cancer Res., 57: 2559-2563, 1997); α-fetoprotein gene promoter (Hallenbeck et al. Hum. Gene Ther., 10: 1721-1733, 1999); the surfactant protein B gene promoter (Doronin et al. J. Virol., 75: 3314-3324, 2001); MUC1 promoter (Kurihara et al. J. Clin. Investig., 106: 763-771, 2000); H19 promoter as per U.S. Pat. No. 8,034,914; those described in issued U.S. Pat. Nos. 7,816,131, 6,897,024, 7,321,030, 7,364,727, and others; etc., as well as derivative forms thereof. In addition, the AIDA-9-Prom and the CCN1 promoter and/or truncated but active versions thereof may be employed. Any promoter that is specific or selective for driving gene expression in cancer cells, or in cells of a particular type of cancer (so as to treat e.g., prostate, colon, breast, etc. primary and metastatic cancer) may be used in the practice of the invention. By "specific for driving gene expression in cancer cells" we mean that the promoter, when operably linked to a gene, functions to promote transcription of the gene only when located within a cancerous, malignant cell, but not when located within normal, non-cancerous cells. By "selective for driving gene expression in cancer cells" we mean that the promoter, when operably linked to a gene, functions to promote transcription of the gene to a greater degree when located within a cancer cell, than when located within non-cancerous cells. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

The transcriptional elements may include other transcription or translation supporting elements such as enhancers, regulatory elements, response elements, etc. and the promoters may be heterologous (not associated with the encoded gene of interest in nature) or homologous (associated with the encoded gene of interest in nature).

Therapy and Administration

Targeted cancer therapy is carried out by administering the constructs, vectors, etc. which encode one or more copies of a recombinant M4 therakine as described herein to a patient in need thereof, or alternatively, administering the M4 protein/polypeptide. M4 therakine may synergize with conventional therapies, including radiation, chemotherapy, monoclonal antibody-based therapy, etc. Thus, M4 may be administered with or without such conventional therapies, or other therapies that are less conventional.

The vector compositions (preparations) of the present invention are typically administered systemically, although this need not always be the case, as localized administration (e.g., intratumoral, or into an external orifice such as the vagina, the nasopharygeal region, the mouth; or into an internal cavity such as the thoracic cavity, the cranial cavity, the abdominal cavity, the spinal cavity, etc.; or peritumorally) is not excluded. For systemic distribution of the vector, the preferred routes of administration include but are not limited to: intravenous, by injection, transdermal, via inhalation or intranasally, or via injection or intravenous administration of a cationic polymer-based vehicle (e.g. in vivo-jetPEI™). Liposomal delivery, which when combined with targeting moieties will permit enhanced delivery. The ultrasound-targeted microbubble-destruction technique (UTMD) may also be used to deliver imaging and theranostic agents (Dash et al. Proc Natl Acad Sci USA. 2011 May 24; 108(21):8785-90. Epub 2011 May 9]; as may hydroxyapatite-chitosan nanocomposites (Venkatesan et al. Biomaterials. 2011 May; 32(15):3794-806); and others (Dash et al. Discov Med. 2011 Jan. 11(56):46-56. Review); etc. Any method that is known to those of skill in the art, and which is commensurate with the type of construct or composition that is employed, may be utilized.

Those of skill in the art will recognize that the amount of a construct or vector that is administered will vary from patient to patient, and possibly from administration to administration for the same patient, depending on a variety of factors, including but not limited to: weight, age, gender, overall state of health, the particular disease being treated, and other factors, and that the amount and frequency of administration is best established by a health care professional such as a physician or oncologist. Typically, optimal or effective tumor-inhibiting or tumor-killing amounts are established e.g. during animal trials and during standard clinical trials. Those of skill in the art are familiar with conversion of doses e.g. from a mouse to a human, which is generally done through body surface area, as described by Freireich et al. (Cancer Chemother Rep 1966; 50(4):219-244); and see Tables I and 2 below, which are taken from the website located at dtp.nci.nih.gov.

TABLE 1

Conversion factors in mg/kg

| | Mouse wt. 20 g | Rat wt 150 g | Monkey wt 3 kg | Dog wt 8 kg | Human wt 60 kg |
|---|---|---|---|---|---|
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | 1⅔ | 1 | ½ |
| Man | 12 | 7 | 3 | 2 | 1 |

For example, given a dose of 50 mg/kg in the mouse, an appropriate dose in a monkey would be 50 mg/kg×¼=13 mg/kg/; or a dose of about 1.2 mg/kg is about 0.1 mg/kg for a human.

TABLE 2

Representative Surface Area to Weight Ratios

| Species | Body Weight (kg) | Surface Area (sq. m.) | Km factor |
|---|---|---|---|
| Mouse | 0.02 | 0.0066 | 3.0 |
| Rat | 0.15 | 0.025 | 5.9 |
| Monkey | 3.0 | 0.24 | 12 |
| Dog | 8.0 | 0.4 | 20 |
| Human, child | 20 | 0.8 | 25 |
| Human, adult | 60 | 1.6 | 37 |

To express the dose as the equivalent mg/sq.m. dose, multiply the dose by the appropriate factor. In adult humans, 100 mg/kg is equivalent to 100 mg/kg×37 kg/sq.m.=3700 mg/sq.m.

In general, for treatment methods, the amount of a vector such as a plasmid will be in the range of from about 0.01 to about 5 mg/kg or from about 0.05 to about 1 mg/kg (e.g. about 0.1 mg/kg), and from about $10^5$ to about $10^{20}$ infectious units (IUs), or from about $10^8$ to about $10^{13}$ IUs for a viral-based vector. In general, for therapy plus imaging methods, the amount of a vector will be in the range of from about 0.01 to about 5 mg/kg or from about 0.05 to about 1 mg/kg (e.g. about 0.1 mg/kg) of e.g. a plasmid, and from about $10^5$ to about $10^{20}$ infectious units (IUs), or from about $10^8$ to about $10^{13}$ IUs for a viral-based vector, Those of skill in the art are familiar with calculating or determining the level of an imaging signal that is required for adequate detection. For example, for radiopharmaceuticals such as [$^{124}$]FIAU, an injection on the order or from about 1 mCi to about 10 mCi, and usually about 5 mCi, (i.e. about 1 mg of material) is generally sufficient.

Further, one type of vector or more than one type of vector may be administered in a single administration, e.g. a therapy vector plus an imaging vector, or two (or more) different therapy vectors (e.g. each of which have differing modes of action so as to optimize or improve treatment outcomes), or two or more different imaging vectors, etc.

In addition, administration of the M4 therakine protein is also encompassed. The protein that is administered is generally "purified" (e.g. substantially purified by removal of other proteins or macromolecules or cellular components or non-physiologically compatible agents introduced during purification) and/or "isolated" using standard techniques known in the art, prior to being combined with the components of an administrable composition as described above. The dosages that are used are those that are generally described above for the protein that is expressed from a vector.

Typically cancer treatment requires repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration once a week for a month) may be followed by a period of no administration for a month, and then followed by a second round of weekly administration for a month, and so on, for any suitable period of time, as required to optimally treat the patient.

In addition, the compositions may be administered in conjunction with other treatment modalities known in the art, such as various chemotherapeutic agents such as Pt drugs and other chemotherapy agents, substances that boost the immune system, antibiotic agents, and the like; and/or with detection and imaging methods (e.g. in conjunction with mammograms, X-rays, Pap smears, prostate specific antigen (PSA) tests, etc. In particular, agents that induce ER stress (unfolded protein response) such as fenretinide and bortezomib (Velcade) may synergize with M4 to enhance therapeutic outcomes.

The subjects or patients to whom the compositions of the invention are administered are typically mammals, frequently humans, but this need not always be the case. Veterinary applications are also contemplated.

The constructs and vectors may also encode one or more additional therapeutic molecules in addition to a recombinant M4 therakine, including but not limited to various suicide genes, including genes encoding various enzymes; oncogenes; tumor suppressor genes; toxins; other cytokines; oncostatins; TRAIL, etc. Exemplary enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); etc. Exemplary tumor suppressor genes include p53, Retinoblastoma tumor suppressor gene (Rb), Wilm's Tumor Gene Product, Phosphotyrosine Phosphatase (PTPase), AdE1A and nm23. Suitable toxins include *Pseudomonas* exotoxin A and S; diphtheria toxin (DT); *E. coli* LT toxins, Shiga toxin, Shiga-like toxins (SLT-1, -2), ricin, abrin, supporin, gelonin, etc. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof. Other anti-tumor agents include: GM-CSF interleukins, tumor necrosis factor (TNF); interferon-beta and virus-induced human Mx proteins; TNF alpha and TNF beta; human melanoma differentiation-associated gene-7 (mda-7), also known as interleukin-24 (IL-24), various other truncated versions of mda-7/IL-24; siRNAs and shRNAs targeting important growth regulating or oncogenes which are required by or overexpressed in cancer cells; antibodies such as antibodies that are specific or selective for attacking cancer cells; etc. When the additional therapeutic agent is TK (e.g. viral TK), a TK substrate such as acyclovir; ganciclovir; various thymidine analogs (e.g. those containing o-carboranylalkyl groups at the 3-position [Al-Madhoun et al., Cancer Res Sep. 1, 2004 64; 6280]) is also administered to the subject. These substrates/drugs act as prodrugs, which in themselves are not toxic, but are converted to toxic drugs by phosphorylation by viral TK. Both the TK gene and substrate are used concurrently to be toxic to the host cancer cell.

Alternatively, if the proteinaceous form of M4 is administered, such agents may be administered together in a composition as described, or separately, e.g., in separate compositions, or encoded by a vector that is co-administered with the protein, etc.

Imaging Plus Treatment

In some embodiments, the invention provides cancer treatment protocols in which treating the disease, e.g. killing, destroying, or otherwise damaging the cancer cells, is combined with imaging of cancer cells and tumors. These protocols may be referred to herein as "theranostics" or "combined therapies" or "combination protocols", or by similar terms and phrases.

In some aspects, the combined therapy involves administering to a cancer patient a vector that encodes, in a single construct, both at least one recombinant M4 therakine (for treating the disease) and a reporter gene (for imaging) the cancer cells that are targeted by the construct. In this embodiment, expression of either a reporter gene or a recombinant M4 therakine gene, or preferably both, is mediated by a cancer cell specific or selective promoter as described herein. Preferably, two different promoters are used in this embodiment in order to prevent or lessen the chance of crossover and recombination within the construct. Alternatively, tandem translation mechanisms may be employed, for example, the insertion of one or more internal ribosomal entry site (IRES) into the construct, which permits translation of multiple mRNA transcripts from a single mRNA. In this manner, both a reporter protein/polypeptide and a recombinant M4 therakine protein/polypeptide that is lethal or toxic to cancer cells are selectively or specifically produced within the targeted cancer cells.

Alternatively, the polypeptides encoded by the constructs of the invention (e.g. plasmids) may be genetically engineered to contain a contiguous sequence comprising a reporter and a recombinant M4 therakine, e.g., separated with an intervening sequence that is cleavable within the cancer cell, e.g., a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived, when measured using standard techniques that are known to those of skill in the art.

In other aspects of combined imaging and therapy, two different vectors may be administered, one of which is an "imaging vector or construct" as described herein, and the other of which is a "recombinant M4 therakine vector or construct" as described herein.

In other aspects of combined imaging and therapy, the genes of interest are encoded in the genome of a viral vector that is capable of transcription and/or translation of multiple mRNAs and/or the polypeptides or proteins they encode, by virtue of the properties inherent in the virus. In this embodiment, such viral vectors are genetically engineered to contain and express genes of interest (e.g., both a reporter gene and at least one recombinant M4 therakine) under the principle control of one or more cancer specific promoters.

In the "therapy plus imaging" aspect of the invention, the vectors/constructs include at least one transcribable element that is either directly detectable using imaging technology, or which functions with one or more additional molecules in a manner that creates a signal that is detectable using imaging technology. The transcribable element is operably linked to a cancer selective/specific promoter as described above, and is generally referred to as a "reporter" molecule. Reporter molecules can cause production of a detectable signal in any of several ways: they may encode a protein or polypeptide that has the property of being detectable in its own right; they may encode a protein or polypeptide that interacts with a second substance and causes the second substance to be detectable; they may encode a protein or polypeptide that sequesters a detectable substance, thereby increasing its local concentration sufficiently to render the surrounding environment (e.g. a cancer cell) detectable. If the gene product of the reporter gene interacts with another substance to generate a detectable signal, the other substance is referred to herein as a "complement" of the reporter molecule.

Examples of reporter proteins or polypeptides that are detectable in their own right (directly detectable) include those which exhibit a detectable property when exposed to, for example, a particular wavelength or range of wavelengths of energy. Examples of this category of detectable proteins include but are not limited to: green fluorescent protein (GFP) and variants thereof, including mutants such as blue, cyan, and yellow fluorescent proteins; proteins which are engineered to emit in the near-infrared regions of the spectrum; proteins which are engineered to emit in the short-, mid-, long-, and far-infrared regions of the spectrum; etc. Those of skill in the art will recognize that such detectable proteins may or may not be suitable for use in humans, depending on the toxicity or immunogenicity of the reagents involved. However, this embodiment has applications in, for example, laboratory or research endeavors involving animals, cell culture, tissue culture, various ex vivo procedures, etc.

Another class of reporter proteins is those, which function with a complement molecule. In this embodiment, a construct comprising a gene encoding a reporter molecule is administered systemically to a subject in need of imaging, and a molecule that is a complement of the reporter is also administered systemically to the subject, before, after or together with the construct. If administered prior to or after administration of the construct, administration of the two may be timed so that the diffusion of each entity into cells, including the targeted cancer cells, occurs in a manner that results in sufficient concentrations of each within cancer cells to produce a detectable signal, e.g. typically within about 1 hour or less. If the two are administered "together", then separate compositions may be administered at the same or nearly the same time (e.g. within about 30, 20, 15, 10, or 5 minutes or less), or a single composition comprising both the construct and the complement may be administered. In any case, no interaction between the reporter and the complement can occur outside of cancer cells, because the reporter is not produced and hence does not exist in any other location, since its transcription is controlled by a cancer specific/selective promoter.

One example of this is the oxidative enzyme luciferase and various modified forms thereof, the complement of which is luciferin. Briefly, catalysis of the oxidation of its complement, luciferin, by luciferase produces readily detectable amounts of light. Those of skill in the art will recognize that this system is not generally used in humans due to the need to administer the complement, luciferin to the subject. However, this embodiment is appropriate for use in animals, and in research endeavors involving cell culture, tissue culture, and various ex vivo procedures.

Another exemplary protein of this type is thymidine kinase (TK), e.g. TK from herpes simplex virus 1 (HSV 1), or from other sources. TK is a phosphotransferase enzyme (a kinase) that catalyzes the addition of a phosphate group from ATP to thymidine, thereby activating the thymidine for incorporation into nucleic acids, e.g., DNA. Various analogs of thymidine are also accepted as substrates by TK, and radiolabeled forms of thymidine or thymidine analogs may be used as the complement molecule to reporter protein TK. Without being bound by theory, it is believed that once phosphorylated by TK, the radiolabeled nucleotides are retained intracellularly because of the negatively charged phosphate group; or, alternatively, they may be incorporated into e.g. DNA in the cancer cell, and thus accumulate within the cancer cell. Either way, they provide a signal that is readily detectable and distinguishable from background radioactivity. Also, the substrate that is bound to TK at the time of imaging provides additional signal in the cancer cell. In fact, mutant TKs with very low Kms for substrates may augment this effect by capturing the substrate. The radioactivity emitted by the nucleotides is detectable using a variety of techniques, as described herein. This aspect of the use of TK harnesses the labeling potential of this enzyme; the toxic capabilities of TK are described below.

Various TK enzymes or modified or mutant forms thereof may be used in the practice of the invention, including but not limited to: HSV1-TK, HSV1-sr39TK, mutants with increased or decreased affinities for various substrates, temperature sensitive TK mutants, codon-optimized TK, the mutants described in U.S. Pat. No. 6,451,571 and US patent application 2011/0136221, both of which are herein incorporated by reference; various suitable human TKs and mutant human TKs, etc.

Detectable TK substrates that may be used include but are not limited to: thymidine analogs such as: "fialuridine" i.e. [1-(2-deoxy-2-fluoro-1-D-arabinofuranosyl)-5-iodouracil], also known as "FIAU" and various forms thereof, e.g. 2'-fluoro-2'-deoxy-β-D-5-[$^{125}$I]iodouracil-arabinofuranoside ([$^{125}$I] FIAU), [$^{124}$I]FIAU; thymidine analogs containing o-carboranylalkyl groups at the 3-position, as described by Al Mahoud et al., (Cancer Res Sep. 1, 2004 64; 6280), which may have a dual function in that they mediate cytotoxicity as well, as described below; hydroxymethyl]butyl)guanine (HBG) derivatives such as 9-(4-$^{18}$F-fluoro-3-[hydroxymethyl]butyl)guanine ($^{18}$F-FHBG); 2'-deoxy-2'-[$^{18}$F]-fluoro-1-beta-D-arabinofuranosyl-5-iodouracil ($^{18}$F-FEAU), 2'-deoxy-2'-[$^{18}$F]-fluoro-5-methyl-1-β-L-arabinofuranosyluracil ($^{18}$F-FMAU), 1-(2'-deoxy-2'-fluoro-beta-D-arabinofuranosyl)-5-[$^{18}$F]iodouracil ($^{18}$F-FIAU), 2'-deoxy-2'-[$^{18}$F]-fluoro-1-beta-D-arabinofuranosyl-5-iodouracil ($^{18}$F-FIAC, see, for example, Chan et al., Nuclear Medicine and Biology 38 (2011) 987-995; and Cai et al., Nuclear Medicine and Biology 38 (2011) 659-666); various alkylated pyrimidine derivatives such as a C-6 alkylated pyrimidine derivative described by Muller et al, (Nucl Med Biol. 2012 February; 39(2):235-46); and others.

Other exemplary reporter molecules may retain or cause retention of a detectably labeled complement by any of a variety of mechanisms. For example, the reporter molecule may bind to the complement very strongly (e.g. irreversibly) and thus increase the local concentration of the complement within cancer cells; or the reporter molecule may modify the complement in a manner that makes egress of the complement from the cell difficult, or at least slow enough to result in a net detectable accumulation of complement within the cell; or the reporter may render the complement suitable for participation in one or more reactions which "trap" or secure the complement, or a modified form thereof that still includes the detectable label, within the cell, as is the case with the TK example presented above.

One example of such a system would be an enzyme-substrate complex, in which the reporter is usually the enzyme and the complement is usually the substrate, although this need not always be the case: the reporter may encode a polypeptide or peptide that is a substrate for an enzyme that functions as the "complement". In some embodiments, the substrate is labeled with a detectable label (e.g. a radio-, fluorescent-, phosphorescent-, calorimetric-, light emitting-, or other label) and accumulates within cancer cells due to, for example, an irreversible binding reaction with the enzyme (i.e. it is a suicide substrate), or because it is released from the enzyme at a rate that is slow enough to result in a detectable accumulation within cancer cells, or the reaction with the enzyme causes a change in the properties of the substrate so that it cannot readily leave the cell, or leaves the cell very slowly (e.g. due to an increase in size, or a change in charge, hydrophobicity or hydrophilicity, etc.); or because, as a result of interaction or association with the enzyme, the substrate is modified and then engages in subsequent reactions which cause it (together with its detectable tag or label) to be retained in the cells, etc.

Other proteins that may function as reporter molecules in the practice of the invention are transporter molecules which are located on the cell surface or which are transmembrane proteins, e.g. ion pumps which transport various ions across cells membranes and into cells. An exemplary ion pump is the sodium-iodide symporter (NIS) also known as solute carrier family 5, member 5 (SLC5A5). In nature, this ion pump actively transports iodide ($I^-$) across e.g. the basolateral membrane into thyroid epithelial cells. Recombinant forms of the transporter encoded by sequences of the constructs described herein may be selectively transcribed in cancer cells, and transport radiolabeled iodine into the cancer cells. Other examples of this family of transporters that may be used in the practice of the invention include but are not limited to norepinephrine transporter (NET); dopamine receptor; various estrogen receptor systems), ephrin proteins such as membrane-anchored ephrin-A (EFNA) and the transmembrane protein ephrin-B (EFNB); epidermal growth factor receptors (EGFRs); insulin-like growth factor receptors (e.g. IGF-1, IGF-2 etc.); transforming growth factor (TGF) receptors such as TGFα; glutamate transporters such as excitatory amino acid transporter 2 (EAAT2), etc. In these cases, the protein or a functional modified form thereof is expressed by the vector of the invention and the ligand molecule is administered to the patient. Usually, the ligand is labeled with a detectable label as described herein, or becomes detectable upon association or interaction with the transporter. In some embodiments, detection may require the association of a third entity with the ligand, e.g. a metal ion. The ligand may also be a protein, polypeptide or peptide.

In addition, antibodies may be utilized in the practice of the invention. For example, the vectors of the invention may be designed to express proteins, polypeptides, or peptides which are antigens or which comprise antigenic epitopes for which specific antibodies have been or can be produced. Exemplary antigens include but are not limited to tumor specific proteins that have an abnormal structure due to mutation (protooncogenes, tumor suppressors, the abnormal products of ras and p53 genes, etc.); various tumor-associated antigens such as proteins that are normally produced in very low quantities but whose production is dramatically increased in tumor cells (e.g. the enzyme tyrosinase, which is elevated in melanoma cells); various oncofetal antigens (e.g. alphafetoprotein (AFP) and carcinoembryonic antigen (CEA); abnormal proteins produced by cells infected with oncoviruses, e.g. EBV and HPV; various cell surface glycolipids and glycoproteins which have abnormal structures in tumor cells; etc. The antibodies, which may be monoclonal or polyclonal, are labeled with a detectable label and are administered to the patient after or together with the vector. The antibodies encounter and react with the expressed antigens or epitopes, which are produced only (or at least predominantly) in cancer cells, thereby labeling the cancer cells. Conversely, the antibody may be produced by the vector of the invention, and a labeled antigen may be administered to the patient. In this embodiment, an antibody or a fragment thereof, e.g. a Fab (fragment, antigen binding) segment, or others that are known to those of skill in the art, are employed. In this embodiment, the antigen or a substance containing antigens or epitopes for which the antibody is specific is labeled and administered to the subject being imaged.

Other examples of such systems include various ligand binding systems such as reporter proteins/polypeptides that bind ligands which can be imaged, examples of which include but are not limited to: proteins (e.g. metalloenzymes) that bind or chelate metals with a detectable signal; ferritin-based iron storage proteins such as that which is described by Iordanova and Ahrnes (Neuroimage. 2012 Jan. 16; 59(2):1004-12.); and others. Such systems of reporter and complement may be used in the practice of the invention, provided that the reporter or the complement can be transcribed under control of a cancer promoter, and that the other binding partner is detectable or can be detectably labeled, is administrable to a subject, and is capable of diffusion into cancer cells. Those of skill in the art will recognize that some such systems are suitable for use, e.g., in human subjects, while other are not due to, for example, toxicity. However, systems in the latter category may be well-suited for use in laboratory settings.

In yet other aspects, the cancer-specific or cancer-selective promoters in the vectors of the invention drive expression of a secreted protein that is not normally found in the circulation. In this embodiment, the presence of the protein may be detected by standard (even commercially available) methods with high sensitivity in serum or urine. In other words, the cancer cells that are detected are detected in a body fluid.

In yet other aspects, the cancer-specific or cancer-selective promoters in the vectors of the invention drive transcription of a protein or antigen to be expressed on the cell surface, which can then be tagged with a suitable detectable antibody or other affinity reagent. Candidate proteins for secretion and cell surface expression include but are not limited to: β-subunit of human chorionic gonadotropin (β hCG); human α-fetoprotein (APP), and streptavidin (SA).

β hCG is expressed in pregnant women and promotes the maintenance of the corpus luteum during the beginning of pregnancy. The level of hCG in non-pregnant normal women and men is 0-5 mIU/mL. hCG is secreted into the serum and urine and β hCG has been used for pregnancy test since the β-subunit of hCG is shared with other hormones. Urine β hCG can be easily detected by a chromatographic immunoassay (i.e. pregnancy test strip, detection threshold is 20-100 mIU/mL) at home-physician's office- and laboratory-based settings. The serum level can be measured by chemiluminescent or fluorescent immunoassays using 2-4 mL of venous blood for more quantitative detection. β hCG has been shown to secreted into the media when it was expressed in monkey cells. Human AFP is an oncofetal antigen that is expressed only during fetal development and in adults with certain types of cancers. AFP in adults can be found in hepatocellular carcinoma, testicular tumors and metastatic liver cancer. AFP can be detected in serum, plasma, or whole blood by chromatographic immunoassay and by enzyme immunoassay for the quantitative measurement.

Streptavidin (SA) can also be used as a cell surface target in the practice of the invention. The unusually high affinity of SA with biotin provides very efficient and powerful target for imaging and therapy. To bring SA to the plasma membrane of the cancer cells, SA can be fused to glycosylphosphatidylinositol (GPT)-anchored signal of human CD14. GPI-anchoring of SA will be suitable for therapeutic applications since GPI-anchor proteins can be endocytosed to the recycling endosomes. Once expressed on the cell surface, SA can then be bound by avidin conjugates that contain a toxic or radiotoxic warhead. Toxic proteins and venoms such as ricin, abrin, *Pseudomonas* exotoxin (PE, such as PE37, PE38, and PE40), diphtheria toxin (DT), saporin, restrictocin, cholera toxin, gelonin, *Shigella* toxin, and pokeweed antiviral protein, *Bordetella pertussis* adenylate cyclase toxin, or modified toxins thereof, or other toxic agents that directly or indirectly inhibit cell growth or kill cells may be linked to avidin; as could toxic low molecular weight species, such as doxorubicin or taxol or radionuclides such as $^{125}$I, $^{131}$I, $^{111}$In, $^{177}$Lu, 211At, $^{225}$Ac, $^{213}$Bi and $^{90}$Y; antiangiogenic agents such as thalidomide, angiostatin, antisense molecules, COX-2 inhibitors, integrin antagonists, endostatin, thrombospondin-1, and interferon alpha, vitaxin, celecoxib, rofecoxib; as well as chemotherapeutic agents such as: pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan), corticosteroids (cortisone, dexamethasone, hydrocortisone, methylprednisolone, prednisone, and prednisolone); growth factor signal transduction kinase inhibitors; mitochondrial dysfunction inducers; caspase activators; and chromatin disruptors, especially those which can be conjugated to nanoparticles The detectable components of the system (usually a complement or substrate) may be labeled with any of a variety of detectable labels, examples of which are described above. In addition, especially useful detectable labels are those which are highly sensitive and can be detected non-invasively, such as the isotopes $^{124}$I, $^{123}$I, $^{99}$mTC, $^{18}$F, $^{86}$Y, $^{11}$C, $^{125}$I, $^{64}$Cu, $^{67}$Ga, $^{68}$Ga, $^{201}$Tl, $^{76}$Br, $^{75}$Br, $^{111}$In, $^{82}$Rb, $^{13}$N, and others.

Those of skill in the art will recognize that many different detection techniques exist which may be employed in the practice of the present invention, and that the selection of one particular technique over another generally depends on the type of signal that is produced and also the medium in which the signal is being detected, e.g. in the human body, in a laboratory animal, in cell or tissue culture, ex vivo, etc. For example, bioluminescence imaging (BLI); fluorescence imaging; magnetic resonance imaging [MRI, e.g. using lysine rich protein (LRp) as described by Gilad et al., Nature Biotechnology, 25, 2 (2007); or creatine kinase, tyrosinase, β-galactosidase, iron-based reporter genes such as transferring, ferritin, and MagA; low-density lipoprotein receptor-related protein (LRP; polypeptides such as poly-L-lysine, poly-L-arginine and poly-L-threonine; and others as described, e.g., by Gilad et al., J. Nucl. Med. 2008; 49(12): 1905-1908); computed tomography (CT); positron emission tomography (PET); single-photon emission computed tomography (SPECT); boron neutron capture; for metals: synchrotron X-ray fluorescence (SXRF) microscopy, secondary ion mass spectrometry (SIMS), and laser ablation inductively coupled plasma mass spectrometry (LA-ICP-MS) for imaging metals; photothermal imaging (using for example, magneto-plasmonic nanoparticles, etc.

For aspects of the invention, which encompass both treatment and imaging, the administration protocols may be any which serve the best interest of the patient. For example, initially, an imaging vector alone may be administered in order to determine whether or not the subject does indeed have cancer, or to identify the locations of cancer cells in a patient that has already been diagnosed with cancer. If cancer is indeed indicated, then compositions with therapeutic vectors are then administered as needed to treat the disease. Usually a plurality of administrations is required as discussed above, and one or more, and sometimes all of these, include at least one imaging vector together with a least one therapeutic vector; or optionally, a single vector with both capabilities. The ability to alternate between therapy and imaging, or to concomitantly carry out both, is a distinct boon for the field of cancer treatment. This methodology allows a medical professional to monitor the progress of treatment in a tightly controlled manner, and to adjust and/or modify the therapy as necessary for the benefit of the patient. For example, administration of a therapeutic and an imaging vector may be alternated; or, during early stages of treatment, initially an imaging vector may be administered, followed by therapy and imaging vectors together until the tumors are no longer visible, followed by imaging vector alone for a period of time deemed necessary to rule out or detect recurrence or latent disease.

Alternatively, if the protein form of M4 is utilized, the other components of the "therapy-imaging" protocol may be administered by a suitable method, e.g., as part of the composition, or as part of a separate composition, or encoded by a vector that is co-administered with the protein composition, etc.

Compositions

The present invention provides compositions, which comprise one or more vectors or constructs as described herein (e.g. encoding at least one or more recombinant M4 therakines) and a pharmacologically suitable (physiologically acceptable) carrier; or which comprise an isolated M4 therakine protein as described herein. The compositions are usually for systemic administration, although local administration (e.g. directly to a tumor) is also encompassed. The preparation of such compositions is known to those of skill in the art. Typically, they are prepared either as liquid solutions or suspensions, or as solid forms suitable for solution in, or suspension in, liquids prior to administration. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any of one or more ingredients known in the art to provide the composition in a form suitable for administration. The final amount of vector or protein in the formulations may vary. However, in general, the amount in the formulations will be from about 1-99%.

Types of Cancer that can be Treated

The methods of treatment and/or of prevention of cancer described herein are not specific for any one type of cancer. However, the cancer cells that are attacked by the recombinant M4 therakine are those which have MDA-7/IL-24 receptors (which occur as dimeric pairs), including but not limited to: IL-20R1/IL-20R2, IL-20R1/IL-22R or IL-22R/IL-20R2, etc. Any type of cancer cell that has such receptors may be targeted and killed or damaged by a recombinant M4 therakine as described herein.

By "cancer" we mean malignant neoplasms in which cells divide and grow uncontrollably, forming malignant tumors, and invade nearby parts of the body. Cancer may also spread or metastasize to more distant parts of the body through the lymphatic system or bloodstream, metastatic cancer may also be prevented or treated. The constructs and methods of the invention may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell cancer, prostate cancer, cervical carcinoma, retinoblastoma, esophageal carcinoma, bladder cancer, neuroblastoma, renal cancer, gastric cancer, pancreatic cancer, and others.

In addition, the invention may also be applied to imaging and therapy of benign tumors, which are generally recognized as not invading nearby tissue or metastasizing, for example, moles, uterine fibroids, etc.

EXAMPLES

Example 1. Construction of a Recombinant M4 Therakine

A secretory signal was added to the M4 fragment of MDA-7/IL-24 using the Flt3 ligand. The procedure involved: A 309-bp cDNA fragment of human MDA-7 (M4) was amplified by PCR using synthetic primers and subcloned into a mammalian expression vector in sense orientation. A 66 bp nucleotide fragment was (Flt3) also added before M4 sequence in sense orientation in the same vector following standard cloning procedures. The resulting constructs are illustrated schematically in FIG. 1.

Example 2. Testing of Recombinant M4 Therakine

Materials and Methods

1. Secretion. IM-PHFA ($2 \times 10^6$) cells were infected with adenovirus expressing either null, Flt3-MDA-7 or Flt3-M4 (5000 vp) in 10-cm plates. Forty-eight hours after infection, the medium was removed, cells were washed with serum free media (SFM) and 4 ml of SFM was added and incubated for further 24 hours. This media was collected and termed as conditioned medium (CM).

2. Western Blot Analysis. IM-PHFA ($2 \times 10^6$) cells were infected with adenovirus expressing either null (empty vector), Flt3-MDA-7 or Flt3-M4 (5000 vp) in 10-cm plates for 48 hours. Conditioned medium (CM) was collected as described above. DU145 or A549 cells ($2 \times 10^6$) were plated overnight and the medium was replaced with 5 ml of either CM collected from IM-PHFA cells or CM collected from Ad-Null, or Ad-Flt3-M4, or Ad-Flt3-MDA-7 infected cells and cultured for 72 hours. This media was replaced with fresh CM after 48 hours. Cells were then collected and used for Western blotting analysis for PARP cleavage.

3. TUNEL Assay. DU145 or A549 cells ($10^4$) were plated overnight in a 4-well chamber slide and the medium was replaced with 1 nil of either CM collected from IM-PHFA cells or CM collected from Ad-Null, Ad-Flt3-M4, or Ad-Flt3-MDA-7 infected cells and cultured for 72 hours. TUNEL assay was performed as per manufacturer's protocols and photomicrographs were taken using fluorescent microscope and representative images are shown.

4. DNA content. DU145 or A549 cells were treated as above, stained with propidium iodide and FACS analysis was performed for DNA content.

5. Analysis of pre- and anti-apoptotic molecules in DU145 and A549 cells after exposure to CM. IM-PHFA ($2 \times 10^6$) cells were infected with adenovirus expressing either Flt3-MDA-7 or Flt3-M4 (5000 vp) in 10-cm plates for 48 hours. Conditioned medium (CM) was collected as described above. DU145 or A549 cells ($2 \times 10^6$) were plated overnight and the medium was replaced with 5 ml of either CM collected from PHFA cells or CM collected from Ad-Flt3-M4, or Ad-Flt3-MDA-7 infected cells and cultured for 72 hours. This media was replaced with fresh conditioned medium after 48 hours. The cells were then collected and used for Western blotting analysis.

6. Tumor volume reduction in viva by Flt3-MDA-7 and Flt3-M4 in subcutaneous tumor cell implants. $2 \times 10^6$ DU145 cells were subcutaneously implanted on both sides of mice. Once the tumors reached measurable size (at least 5-mm), left flank tumors were infected with $2 \times 10^8$ viral particles of either Flt3-MDA-7 or Flt3-M4 3× every alternate day and observed for tumor regression. $2 \times 10^6$ DU-145 cells were subcutaneously implanted on the left side and $5 \times 10^6$ A549 cells were implanted on the right side (5 days prior to DU145 cell implantation to maintain equal tumor sizes). Once the tumors reached measurable sizes, left flank tumors were treated with $2 \times 10^8$ viral particles of either Flt3-MDA-7 or Flt3-M4 3× every alternate day and observed for tumor regression.

Results

The results showed that the recombinant therakine is secreted (FIG. 2) and displays "bystander" activity equivalent to that of native MDA-7/IL-24 (FIG. 3). In addition, like MDA-7/IL-24, the recombinant M4 therakine induced production of SARI (Suppressor of AP-1, regulated by Interferon), which is required for cell killing by mda-7/IL-24 (FIG. 4). In addition, when tested in an animal model, both direct and distant cancer cell killing was exhibited (see FIGS. 5A and B).

These results show that Flt3-M4, an exemplary truncated, modified version of mda-7/IL-24, exhibits both direct and distant killing of cancer cells at levels similar to those of the full-length gene product, and that these activities are exhibited both in vitro and in vivo. The novel recombinant M4 therakines described herein thus represent new therapeutic molecules for the treatment of diverse cancers.

Example 3. Further Testing of M4

The ability of MDA-7/IL-24 and M4 to promote "bystander" activity was assessed. Subcutaneously implanted tumors in the left side were treated with $2 \times 10^8$ viral particles of either Flt3-M4 or Flt3-MDA-7 3× every alternate day and observed for tumor regression.

Figure 6:
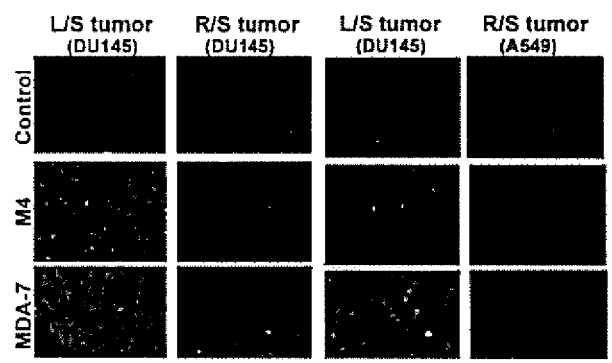
FIG. 6. TUNEL, staining showing bystander effect of secreted MDA-7 and M4 in untreated receptor positive distant DU145 tumors, but not in receptor negative A549 tumors.

To evaluate the apoptotic (cell death) response of Flt3-MDA-7 or Flt3-M4, TUNEL assays were done according to the manufacturer's protocol in paraffin-embedded tumor tissue sections. The slides were observed for TUNEL positive staining (green florescence) under a florescence microscope and photographed. TUNEL results are presented in FIG. 6. As can be seen, secreted MDA-7/IL-24 and M4 promote profound "bystander" activity (evidenced by TUNEL staining) in untreated distant right side receptor positive DU145 tumors, but not in receptor negative A549 tumors.

Figure 7:
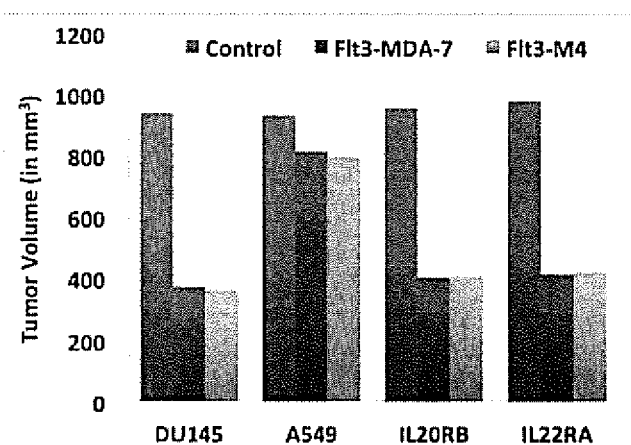
FIG. 7. Graphical representation of "bystander" activity of secreted MDA-7/IL-24 and M4 in tumors arising from implanted DU145 cells, A549 receptor negative cells, and receptor positive A549 (cells reconstituted with IL20 or IL22).

A549 cells express IL20R1 endogenously, but do not express a second member of the dimeric receptor pair that is required for MDA-7/IL-24 activity. Hence, to test bystander activity, IL20R2 and IL22R (labeled IL22RA and IL20RB in FIG. 7, respectively) were overexpressed in A549 cells to reconstitute a dimeric receptor and the ability of Flt3-MDA-7 or Flt3-M4 to exert "bystander" activity on untreated right side tumors generated by implanting these and receptor positive DU145 cells. The results are presented in FIG. 7. As can be seen, tumor volume was reduced in DU145 tumors and in A549 tumors with reconstituted dimeric receptors, but not in A549 receptor negative cells.

The ability of secreted MDA-7/IL-24 and M4 to induce apoptosis in IL-20/IL-22 receptor positive cells was tested. IM-PHFA ($2 \times 10^6$) cells were infected with adenovirus expressing either null, Flt3-MDA-7 or Flt3-M4 (5000 vp) in 10-cm plates for 48 hours. Conditioned media (CM) was collected as described above. A549 cells ($2 \times 10^6$) (receptor negative) or A549 IL-20R2/A549 IL-22R (receptor reconstituted cells) were plated overnight and the medium was replaced with 5 ml of either CM collected from Ad-Null, or Ad-Flt3-M4, or Ad-Flt3-MDA-7 infected cells and cultured for 72 hours. This media was replaced with fresh conditioned medium after 48 hours. Cells were then collected and used for Western blotting analysis for PARP cleavage. All the experiments were repeated at least three times and representative images are shown.

Figure 8:
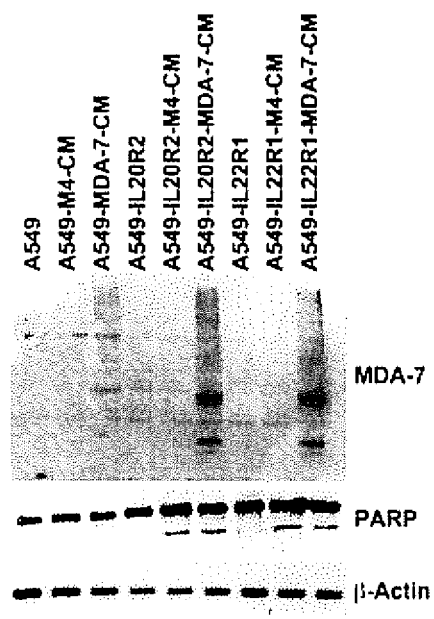
FIG. 8. Secreted MDA-7/IL-24 and M4 induces apoptosis in IL-20/IL-22 receptor positive cells. 1M-PHFA (2×10$^6$) cells were infected with adenovirus expressing either null, Flt3-MDA-7 or Flt3-M4 (5000 vp) in 10 cm plates for 48 hours. Conditioned media (CM) was collected as described in FIG. 2. A549 cells (2×10$^6$) (Receptor negative) or A549 IL-20R2/A549 IL-22R1 (receptor reconstituted cells) were plated overnight and the medium was replaced with 5 ml of either CM collected from Ad-Null, or Ad-Flt3-M4, or Ad-Flt3-MDA-7 infected cells and cultured for 72 hours. This media was replaced with fresh conditioned medium after 48 hours. Cells were then collected and used for western blotting analysis for PARP cleavage. All the experiments were repeated at least three times and representative images are shown.

The results are presented in FIG. 8. As can be seen, secreted MDA-7/IL-24 and M4 induce apoptosis in IL-20/IL-22 receptor positive cells.

Example 4. Purified M4 Protein

Purified His-M4 was generated as follows: IM-PHFA cells (hTERT-immortalized primary human fetal astrocytes) were infected with either Ad.His-F13-MDA-7 or Ad.His-Flt-3-M4 and cultured for 72 hours in medium. Once cell detachment from the culture vessel was noted the medium containing secreted His-MDA-7 or His-M4, respectively, was collected. The collected medium was centrifuged and cell debris were removed. The collected medium was mixed with binding buffer (50 mM NaH$_2$PO4 (pH 8.0), 150 mM NaCl, 5 mM Imidazole, 5% glycerol, 0.05% Tween-20) and with Ni-NTA slurry and incubated over night to allow His-MDA-7 or His-M4 to bind to the Ni slurry. The slurry with the medium was then passed through the column and allowed to drain completely. The slurry in the column was washed 3 times with wash buffer (50 mM NaH$_2$PO4 (pH 8.0), 300 mM NaCl, 10 mM. Imidazole, 5% glycerol, 0.05% Tween-20). After washing the slurry was incubated with 5 nil of elution buffer (50 mM NaH$_2$PO$_4$ (pH 8.0), 300 mM NaCl, 400 mM Imidazole, 5% glycerol, 0.05% Tween-20) for 2-3 hours. The eluent was collected and concentrated using 3 KDa cut-off membrane.

Figure 9:
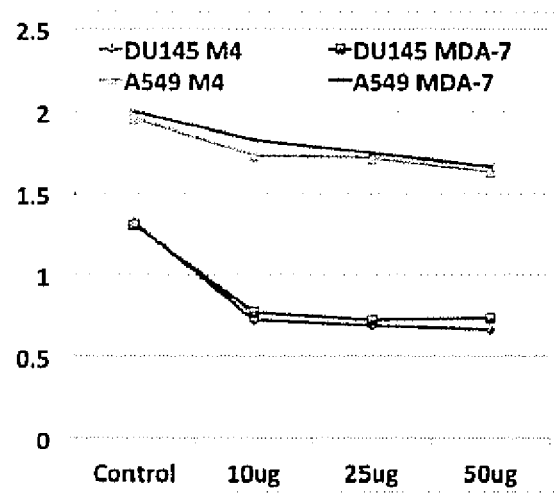
FIG. 9. His-M4 or His-MDA-7 pure protein shows receptor-mediated biological activity in cancer cells. A549 (without a complete dimeric receptor pair) or DU145 cells (dimeric receptor positive) were cultured for 24 hours (~60-70% confluence), cells were then trypsinized and plated in each well of 96-well plate. 8 wells for each treatment were used for performing MTT assays. The cells were treated either with His-M4 or His-MDA-7 at the indicated doses (reconstituted lyophilized protein) and cultured for an additional 96 hours and MTT assays were performed according to the standard protocol. Experiments were repeated at least three times and representative line graph are shown. These results indicate that His-M4 or His-MDA-7 exert equal biological activity in a receptor-dependent manner in cancer cells.
Figure 10:
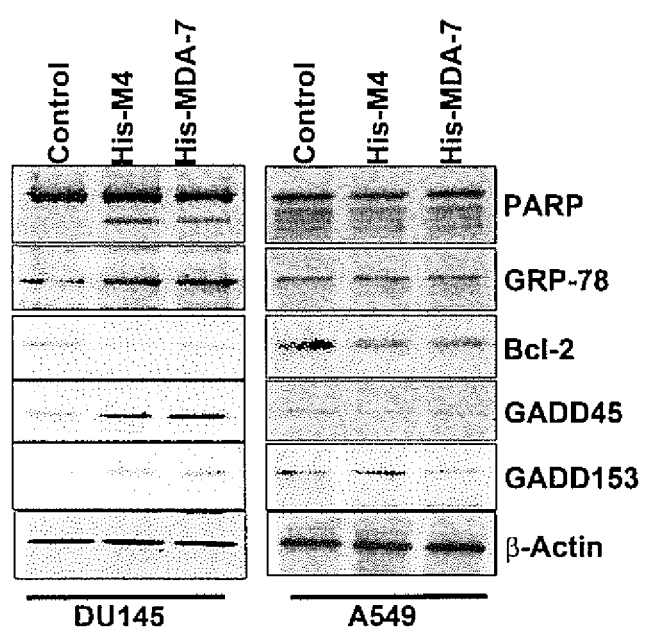
FIG. 10. His-M4 or His-MDA-7 pure protein induces PARP cleavage and ER stress markers. DU145 or A549 cells were cultured for 24 hours (~50-60% confluence), and treated with 10 µg/ml of His-M4 or His-MDA-7 and cultured for an additional 96 hours. Cell lysates were subjected to western blotting analysis for PARP, GRP-78, Bcl2, GADD45 and GADD153 protein expression using specific antibodies.

His-M4 exerts significant growth inhibitory effects on receptor positive cancer cells (such as DU145), but not in receptor complex negative cells (such as A549), in a similar manner as His-MDA-7 (FIG. 9). Treatment with these pure proteins was associated with induction of PARP cleavage, and ER stress markers, but only in the receptor positive DU145 cells (FIG. 10).

Example 5

Comparative testing of the two cytokines M4 and MDA-7/IL-24 is carried out for different properties in serum relative to half-life, bioactivity based on concentration, bioavailability, tissue distribution, etc. The growth inhibitory properties and signaling effects of His-M4 are found to be comparable to those of His-MDA-7.

The invention can be practiced with modification within the spirit and scope of the appended claims. Accordingly, the present invention should not be limited to the embodiments as described above, but should further include all modifications and equivalents thereof within the spirit and scope of the description provided herein.

The complete contents of all patents, patent applications and publications cited herein are hereby incorporated by reference in entirety.

REFERENCES

Dash R, Bhoopathi P, Das S K, Sarkar S, Emdad L, Dasgupta S, Sarkar D, Fisher P B. Novel mechanism of MDA-7/IL-24 cancer-specific apoptosis through SARI induction. Cancer Res. 2014; 74: 563-574.

Dash R, Bhutia S K, Azab B, Su Z Z, Quinn B A, Kegelmen T P, Das S K, Kim K, Lee S G, Park M A, Yacoub A, Rahmani M, Emdad L, Dmitriev I P, Wang X Y, Sarkar D, Grant 5, Dent P, Curiel D T, Fisher P B, mda-7/IL-24: a unique member of the IL-10 gene family promoting cancer-targeted toxicity. Cytokine Growth Factor Rev, 2010; 21: 381-391.

Emdad L, Lebedeva I V, Su Z Z, Sarkar D, Dent P, Curiel D T, Fisher P B. Melanoma differentiation associated gene-7/interleukin-24 reverses multidrug resistance in human colorectal cancer cells. Mol Cancer Ther. 2007; 6: 2985-2994.

Fisher P B. Is mda-7/IL-24 a "magic bullet" for cancer? Cancer Res. 2005; 65: 10128-38.

Fisher P B, Sarkar D, Lebedeva I V, Emdad L, Gupta P, Sauane M, Su Z Z, Grant S, Dent P, Curiel D T, Senzer N, Nemunaitis J. Melanoma differentiation associated gene-7/interleukin-24 (mda-7/IL-24): novel gene therapeutic for metastatic melanoma. Toxicol Appl Pharmacol. 2007; 224: 300-307.

Gao P, Sun X, Chen X, Wang Y, Foster B A, Subjeck J, Fisher P B, Wang X Y. Secretable chaperone Grp170 enhances therapeutic activity of a novel tumor suppressor, mda-7/IL-24. Cancer Res. 2008; 68: 3890-3898.

Gupta P, Walter M R, Su Z Z, Lebedeva I V, Emdad L, Randolph A, Valerie K, Sarkar D, Fisher P B. BiP/GRP78 is an intracellular target for MDA-7/IL-24 induction of cancer-specific apoptosis. Cancer Res. 2006; 66: 8182-8191.

Jiang H, and Fisher P B. Use of a sensitive and efficient subtraction hybridization protocol for the identification of genes differentially regulated during the induction of differentiation in human melanoma cells. Mol Cell Differ. 1993; 1: 285-299.

Jiang H, Lin J J, Su Z Z, Goldstein N I, Fisher P B. Subtraction hybridization identifies a novel melanoma differentiation associated gene, mda-7, modulated during human melanoma differentiation, growth and progression. Oncogene. 1995; 11: 2477-2486.

Jiang H, Su Z Z, Lin J J, Goldstein N I, Young C S, Fisher P B. The melanoma differentiation associated gene mda-7 suppresses cancer cell growth. Proc Natl Acad Sci USA. 1996; 93: 9160-9165.

Lebedeva I V, Su Z Z, Vozhilla N, Chatman L, Sarkar D, Dent P, Athar M, Fisher P B. Mechanism of in vitro pancreatic cancer cell growth inhibition by melanoma differentiation-associated gene-7/interleukin-24 and perillyl alcohol. Cancer Res. 2008; 68: 7439-7447.

Ramesh R, Mhashilkar A M, Tanaka F, Saito Y, Branch C D, Sieger K, Mumm J B, Stewart A L, Boquoi A, Dumoutier L, Grimm E A, Renauld J C, Kotenko S, Chada S. Melanoma differentiation-associated gene 7/interleukin (IL)-24 is a novel ligand that regulates angiogenesis via the IL-22 receptor. Cancer Res. 2003; 63:5105-5113.

Sarkar D, Lebedeva I V, Gupta P, Emdad L, Sauane M, Dent P, Curiel D T, Fisher P B. Melanoma differentiation associated gene-7 (mda-7)/IL-24: a 'magic bullet' for cancer therapy? Expert Opin Biol Ther. 2007a; 7: 577-586.

Sarkar D, Lebedeva I V, Su Z Z, Park E S, Chatman L, Vozhilla N, Dent P, Curiel D T, Fisher P B. Eradication of therapy-resistant human prostate tumors using a cancer terminator virus. Cancer Res. 2007b; 67:5434-5442.

Sauane M, Gupta P, Lebedeva I V, Su Z Z, Sarkar D, Randolph A, Valerie K, Gopalkrishnan R V, Fisher P B. N-glycosylation of MDA-7/IL-24 is dispensable for tumor cell-specific apoptosis and "bystander" antitumor activity. Cancer Res. 2006; 66: 11869-11877.

Sauane M, Su Z Z, Gupta P, Lebedeva I V, Dent P, Sarkar D, Fisher P B. Autocrine regulation of mda-7/IL-24 mediates cancer-specific apoptosis. Proc Natl Acad Sci USA. 2008; 105:9763-9768.

Su Z, Emdad L, Sauane M, Lebedeva I V, Sarkar D, Gupta P, James C D, Randolph A, Valerie K, Walter M R, Dent P, Fisher P B. Unique aspects of mda-7/IL-24 antitumor bystander activity: establishing a role for secretion of MDA-7/IL-24 protein by normal cells. Oncogene. 2005; 24: 7552-7566.

Su Z Z, Lee S G, Emdad L, Lebedeva I V, Gupta P, Valerie K, Sarkar D, Fisher P B. Cloning and characterization of SARI (suppressor of AP-1, regulated by IFN). Proc Natl Acad Sci USA. 2008; 105:20906-20911.

Su Z Z, Madireddi M T, Lin J J, Young C S, Kitada S, Reed J C, Goldstein N I, Fisher P B. The cancer growth suppressor gene mda-7 selectively induces apoptosis in human breast cancer cells and inhibits tumor growth in nude mice. Proc Natl Acad Sci USA. 1998; 95: 14400-14405.

Tong A W, Nemunaitis J, Su D, Zhang Y, Cunningham C, Senzer N, Netto G, Rich D, Mhashilkar A, Parker K, Coffee K, Ramesh R, Ekmekcioglu S, Grimm E A, van Wart Flood J, Merritt J, Chada S. Intratumoral injection of INGN 241, a nonreplicating adenovector expressing the melanoma-differentiation associated gene-7 (mda-7/IL24): biologic outcome in advanced cancer patients. Mol Ther. 2005; 11:160-172.

Yacoub A, Flamed Emdad L, Dos Santos W, Gupta P, Broaddus W C, Ramakrishnan V, Sarkar D, Shah K, Curiel D T, Grant S, Fisher P B, Dent P. MDA-7/IL-24 plus radiation enhance survival in animals with intracranial primary human GBM tumors. Cancer Biol Ther. 2008 June; 7(6):917-33.

We claim:

1. A recombinant cytokine comprising:
   i) a fragment of MDA-7/IL-24 that has antitumor activity and interacts with MDA-7/IL-24 receptors on the surface of cancer cells; and
   ii) a heterologous secretory leader sequence, wherein:
   a) said heterologous secretory leader sequence comprises SEQ ID NO: 3, or
   b) said recombinant cytokine comprises SEQ ID NO: 5.

2. The recombinant cytokine of claim 1, wherein said fragment of MDA-7/IL-24 comprises SEQ ID NO: 1.

* * * * *

SEQUENCE LISTING

```
<160> NUMBER OF SEQ ID NOS: 6

<210> SEQ ID NO 1
<211> LENGTH: 103
<212> TYPE: PRT
<213> ORGANISM: Artificial Sequence
<220> FEATURE:
```

-continued

<223> OTHER INFORMATION: Synthetic cytokine

<400> SEQUENCE: 1

Glu Ser Cys Tyr Leu Val His Thr Leu Leu Glu Phe Tyr Leu Lys Thr
1               5                   10                  15

Val Phe Lys Asn Tyr His Asn Arg Thr Val Glu Val Arg Thr Leu Lys
            20                  25                  30

Ser Phe Ser Thr Leu Ala Asn Asn Phe Val Leu Ile Val Ser Gln Leu
        35                  40                  45

Gln Pro Ser Gln Glu Asn Glu Met Phe Ser Ile Arg Asp Ser Ala His
    50                  55                  60

Arg Arg Phe Leu Leu Phe Arg Arg Ala Phe Lys Gln Leu Asp Val Glu
65                  70                  75                  80

Ala Ala Leu Thr Lys Ala Leu Gly Glu Val Asp Ile Leu Leu Thr Trp
                85                  90                  95

Met Gln Lys Phe Tyr Lys Leu
            100

<210> SEQ ID NO 2
<211> LENGTH: 312
<212> TYPE: DNA
<213> ORGANISM: Artificial Sequence
<220> FEATURE:
<223> OTHER INFORMATION: Snythetic nucleic acid sequence encoding
      truncated cytokine

<400> SEQUENCE: 2
gagagctgtt accttgtcca caccctgctg gagttctact tgaaaactgt tttcaaaaac     60
taccacaata gaacagttga agtcaggact ctgaagtcat tctctactct ggccaacaac    120
tttgttctca tcgtgtcaca actgcaaccc agtcaagaaa atgagatgtt ttccatcaga    180
gacagtgcac acaggcggtt tctgctattc cggagagcat tcaaacagtt ggacgtagaa    240
gcagctctga ccaaagccct tggggaagtg gacattcttc tgacctggat gcagaaattc    300
tacaagctct ga                                                        312

<210> SEQ ID NO 3
<211> LENGTH: 23
<212> TYPE: PRT
<213> ORGANISM: Artificial Sequence
<220> FEATURE:
<223> OTHER INFORMATION: Synthetic secretory signal sequence

<400> SEQUENCE: 3

Met Thr Val Leu Ala Pro Ala Trp Ser Pro Thr Thr Tyr Leu Leu Leu
1               5                   10                  15

Leu Leu Leu Leu Ser Gly Ser
            20

<210> SEQ ID NO 4
<211> LENGTH: 69
<212> TYPE: DNA
<213> ORGANISM: Artificial Sequence
<220> FEATURE:
<223> OTHER INFORMATION: Snythetic nucleic acid sequence encoding
      secretory signal sequence

<400> SEQUENCE: 4
atgacagtgc tggcgccagc ctggagccca acaacctatc tcctcctgct gctgctgctg     60
agcggatcc                                                             69

```
<210> SEQ ID NO 5
<211> LENGTH: 126
<212> TYPE: PRT
<213> ORGANISM: Artificial Sequence
<220> FEATURE:
<223> OTHER INFORMATION: Snythetic cytokine with secretory signal
      sequence

<400> SEQUENCE: 5

Met Thr Val Leu Ala Pro Ala Trp Ser Pro Thr Thr Tyr Leu Leu Leu
1               5                   10                  15

Leu Leu Leu Ser Gly Ser Glu Ser Cys Tyr Leu Val His Thr Leu
            20                  25                  30

Leu Glu Phe Tyr Leu Lys Thr Val Phe Lys Asn Tyr His Asn Arg Thr
            35                  40                  45

Val Glu Val Arg Thr Leu Lys Ser Phe Ser Thr Leu Ala Asn Asn Phe
        50                  55                  60

Val Leu Ile Val Ser Gln Leu Gln Pro Ser Gln Glu Asn Glu Met Phe
65                  70                  75                  80

Ser Ile Arg Asp Ser Ala His Arg Arg Phe Leu Leu Phe Arg Arg Ala
                85                  90                  95

Phe Lys Gln Leu Asp Val Glu Ala Ala Leu Thr Lys Ala Leu Gly Glu
                100                 105                 110

Val Asp Ile Leu Leu Thr Trp Met Gln Lys Phe Tyr Lys Leu
            115                 120                 125

<210> SEQ ID NO 6
<211> LENGTH: 381
<212> TYPE: DNA
<213> ORGANISM: Artificial Sequence
<220> FEATURE:
<223> OTHER INFORMATION: Synthetic nucleic acid sequence encoding
      recombinant cytokine wtih secretory signal sequence

<400> SEQUENCE: 6
atgacagtgc tggcgccagc ctggagccca acaacctatc tcctcctgct gctgctgctg       60
agcggatccg agagctgtta ccttgtccac accctgctgg agttctactt gaaaactgtt      120
ttcaaaaact accacaatag aacagttgaa gtcaggactc tgaagtcatt ctctactctg      180
gccaacaact tgttctcat cgtgtcacaa ctgcaaccca gtcaagaaaa tgagatgttt       240
tccatcagag acagtgcaca caggcggttt ctgctattcc ggagagcatt caaacagttg      300
gacgtagaag cagctctgac caaagcccctt ggggaagtgg acattcttct gacctggatg     360
cagaaattct acaagctctg a                                                 381
```